(12) United States Patent
Larue et al.

(10) Patent No.: US 10,588,280 B2
(45) Date of Patent: Mar. 17, 2020

(54) AIDED DELIVERY OF PLANT TREATMENT AGENTS

(71) Applicant: Monsanto Technology LLC, St. Louis, MO (US)

(72) Inventors: Huachun Larue, St. Louis, MO (US); Fenggao Dong, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 222 days.

(21) Appl. No.: 15/308,249

(22) PCT Filed: May 1, 2015

(86) PCT No.: PCT/US2015/028955
§ 371 (c)(1),
(2) Date: Nov. 1, 2016

(87) PCT Pub. No.: WO2015/168659
PCT Pub. Date: Nov. 5, 2015

(65) Prior Publication Data
US 2017/0055475 A1    Mar. 2, 2017

Related U.S. Application Data

(60) Provisional application No. 61/987,260, filed on May 1, 2014.

(51) Int. Cl.
*A01H 1/08* (2006.01)
(52) U.S. Cl.
CPC .................................... *A01H 1/08* (2013.01)
(58) Field of Classification Search
None
See application file for complete search history.

(56) References Cited

U.S. PATENT DOCUMENTS

| | | | |
|---|---|---|---|
| 3,882,634 A | 5/1975 | Dedolph | |
| 4,945,050 A * | 7/1990 | Sanford | C12M 35/04 435/243 |
| 5,866,513 A | 2/1999 | Michelotti et al. | |
| 7,902,426 B1 | 3/2011 | Hiei et al. | |
| 2010/0169999 A1 | 7/2010 | Cui et al. | |

OTHER PUBLICATIONS

He et al (Biomolecule delivery into canola protoplasts by centrifuging cells with microbubbles. FEBS Letters 587: 285-290, Published online Dec. 19, 2012).*
Lim et al (Protoplast Isolation and Regeneration of Fertile Plants from *Arabidopsis* Trp Mutant, trp1-100. Korean J Bid Sci 2: 239-242 1998).*
Molnar et al (Small Silencing RNAs in Plants Are Mobile and Direct Epigenetic Modification in Recipient Cells. Science, vol. 328, 872-875, May 14, 2010).*
Duivenvoorden, "A Centrifugation Method for Determining the Fresh Weight of Aquatic Macrophytes", Aquatic Botany, 1987, pp. 275-282, vol. 29.
"9th Compendium of Herbicide Adjuvants", 2016, 13th Edition.
Abendroth et al., "Plant Development and Staging Methods", Corn Growth and Development, PMR 1009, Mar. 2011, pp. 4-7.
Bordes et al., "Haplodisploidization of Maize (*Zea mays* L) Through Induced Gynogenesis Assisted by Glossy Markers and Its Use in Breeding", Agronomie, 1997, pp. 291-297, vol. 17.
Chalyk et al., "Transgressive Segregation in the Progeny of a Cross Between Two Induces of Maize Maternal Haploids", 2000, retrieved from <http://www.agron.missouri.edu/mnl/68/69chalyk.html> on Sep. 7, 2017, 2 pages.
Chalyk, "Obtaining Fertile Pollen in Maize Maternal Haploids", 2000, retrieved from <http://www.agron.missouri.edu/mnl/74/93chalyk.html> on Sep. 7, 2017, 3 pages.
Chalyk, "Properties of Maternal Haploid Maize Plants and Potential Application to Maize Breeding", Euphytica, 1994, pp. 13-18, vol. 79.
Chang et al., "Chapter 10—Doubled Haploids", Molecular Genetic Approaches to Maize Improvement, Biotechnology in Agriculture and Forestry, 2009, pp. 127-142, vol. 63.
Coe, "A Line of Maize With High Haploid Frequency", The American Naturalist, 1959, pp. 381-382, vol. 93, No. 873.
Deimling et al., "Methodology and Genetics of In Vivo Haploid Induction in Maize", Vort. Pflanzenzuchtg., 1997, pp. 203-224, vol. 38, with uncertified machine translation into English.
Eder et al., "In Vivo Haploid Induction in Maize", Theoretical and Applied Genetics, 2002, pp. 703-708, vol. 104.
Forster et al., "Doubled Haploids in Genetics and Plant Breeding", Plant Breeding Reviews, 2005, pp. 57-88, vol. 25.
Gayen et al., "Chromosome Doubling in Haploids Through Colchicine", 1994, retrieved from <http://www.agron.missouri.edu/mnl/68/101gayen.html> on Sep. 7, 2017, 2 pages.
Geiger et al., "Doubled Haploids in Hybrid Maize Breeding", Maydica, 2009, pp. 485-499, vol. 54.
Geiger, "Doubled Haploids", Maize Handbook—Volume II: Genetics and Genomics, 2009, pp. 641-657.
Han et al., "Study on Identifying Methods of Maize Haploid Induced by Stock6", Journal of Maize Sciences, 2006, pp. 64-66, 69, vol. 14, No. 1, English Abstract.
Röber et al., "In Vivo Haploid Induction in Maize—Performance of New Inducers and Significance of Doubled Haploid Lines in Hybrid Breeding", Maydica, 2005, pp. 275-283, vol. 50.
Szarejko et al., "Doubled Haploidy and Induced Mutation", Euphytica, 2007, pp. 359-370, vol. 158.

* cited by examiner

*Primary Examiner* — Medina A Ibrahim
*Assistant Examiner* — Wayne Zhong
(74) *Attorney, Agent, or Firm* — Thompson Coburn LLP; William A. Holtz; Jamie Davis

(57) ABSTRACT

Provided herein are delivery methods of a plant treatment agent to a tissue of a plant, wherein the tissue is contacted with a plant treatment agent and delivery is aided by a centrifugal force applied to the plant. Disclosed herein is the discovery that drastic improvements in treatment delivery occur when plants are centrifuged after being contacted, submerged, unsubmerged, soaked, etc. in a solution containing a plant treatment agent. In one embodiment, haploid plants contacted with a colchicine solution are centrifuged to reveal improved chromosomal doubling rates as compared to control plants.

19 Claims, 9 Drawing Sheets

| | Stage | Common Name |
|---|---|---|
| Vegatative | VE | Emergence |
| | V1 | First Leaf |
| | V2 | Second Leaf |
| | V3 | Third Leaf |
| | ... | ... |
| | Vn | nth Leaf |
| | VT | Tasseling |
| Reproductive | R1 | Silking |
| | R2 | Blister |
| | R3 | Milk |
| | R4 | Dough |
| | R5 | Dent |
| | R6 | Physiological Maturity |

Figure 2

| Vegetative Development Staging Methods | | | Growth Measurements | |
|---|---|---|---|---|
| Leaf Collar | Horizontal Leaf | Leaf Tip | Extended Leaf Height | Canopy Plant Height |
| | | | Inches | |
| V1 | NA* | 3.5 | 4 | 3 |
| V2 | 3.0 | 5.0 | 6 | 4 |
| V3 | 4.5 | 6.5 | 10 | 7 |
| V4 | 5.5 | 8.0 | 15 | 10 |
| V5 | 6.5 | 9.0 | 21 | 14 |
| V6 | 8.0 | 10.5 | 28 | 19 |
| V7 | 9.0 | 12.0 | 35 | 24 |
| V8 | 10.0 | 13.0 | 43 | 31 |
| V9 | 11.5 | 14.5 | 52 | 39 |
| V10 | 12.5 | 15.5 | 60 | 47 |
| V11 | 13.0 | 16.5 | 66 | 53 |
| V12 | 13.5 | 17.0 | 72 | 60 |
| V13 | 14.0 | 17.5 | 78 | 66 |
| V14 | 15.0 | 18.0 | 84 | 73 |
| V15 | 15.5 | NA** | 89 | 80 |
| V16 | NA* | NA** | 94 | 87 |
| V17 | NA* | NA** | 99 | 93 |
| V18 | NA* | NA** | 103 | 100 |
| V19 | NA* | NA** | 106 | 103 |
| V20 | NA* | NA** | 107 | 105 |

Figure 3

AIDED DELIVERY OF PLANT TREATMENT AGENTS

CROSS-REFERENCE TO RELATED APPLICATIONS

This application is a 35 U.S.C. § 371 U.S. National Phase Application of International Patent Application No. PCT/US2015/028955, filed May 1, 2015, which claims the benefit of U.S. Provisional Patent Application No. 61/987,260, filed on May 1, 2014, both of which are incorporated herein by reference in their entireties.

BACKGROUND

Reliable and effective control of plant development, including growth and reproduction, continues to be a challenge for plant scientists. One way to accomplish this control is to apply various plant treatment agents that cause plants to exhibit desired characteristics. Unfortunately, this is often only a reliable method when the treatment thoroughly contacts one or more specific tissues that are difficult to reach, such as tissues inside of the plant.

Soaking plants for a prolonged period can deliver some agents to desired tissues. However, this approach often leads to undesired effects, such as increased mortality due to the agent being toxic to the plant in a prolonged or non-specific exposure.

The use of doubled haploids (DH) allows breeders to generate completely homozygous and homogenous lines in fewer generations than traditional backcrossing (Eder and Chalyk, 2002; Röber et al., 2005; Chang and Coe, 2009; Geiger, 2009). DH techniques have been developed for over 250 crop species (Forster and Thomas, 2005) and DH lines have been used for structural and functional genomics, marker-trait association studies, and molecular cytogenetics (Chang and Coe, 2009; Geiger, 2009). Incorporating DH technologies in a plant breeding pipeline can increase efficacy of selection (Röber et al., 2005; Geiger, 2009; Geiger and Gordillo, 2009), reduce breeding cycle length (Szarejko and Forster, 2007; Chang and Coe, 2009; Geiger and Gordillo, 2009), and reduce efforts required for line maintenance (Röber et al., 2005).

Although spontaneous chromosome doubling occurs, the frequency is so low (typically less than 5%), that researchers attempting to create doubled haploids plants (collectively termed DH) often subject haploid plants to a treatment that promotes chromosome doubling. Haploid seedlings subjected to a chromosome doubling treatment (termed $DH_0$ plants) can produce haploid egg and/or sperm, and if the $DH_0$ plants are successfully selfed, the zygotic chromosome number can be recovered in substantially homozygotic offspring (termed $DH_1$ plants) that exhibit the vigor and fertility expected of 2n sporophytes.

A common method of artificially triggering chromosome doubling is to apply the anti-microtubule agent colchicine (Chase, 1952, 1969; Gayen et al., 1994; Bordes et al., 1997; Chalyk, 2000; Eder and Chalyk, 2002; Han et al., 2006). However, this was considered an unreliable approach because the effects were often genotype specific (Geiger, 2009) and the concentrations of colchicine needed to bring about improved doubling rates proved to be toxic to treated seedlings (Jensen, 1974). Today, institutions attempting to provoke chromosome doubling are actively exploring treatments which are less toxic to plant tissue and less dangerous to human technicians conducting the treatments (Geiger and Gordillo, 2009).

Gayen et al. (1994) removed the tips of seedling coleoptiles and subjected the remaining body of the seedlings to an extended (6+ hours) soak in a low colchicine concentration (0.1% or less) to generate a doubling rate of 18.05%. Deimling et al. (1997) improved this method by waiting to remove tips until the coleoptiles were at least 1 cm long and soaking the plants in 0.06% colchicine and DMSO for 12 hours in a dark room. Eder and Chalyk (2002) demonstrated that this procedure works on a range of genotypes, with an average success rate of nearly 50%. However, none of these methods are amenable to the sort of high-throughput processes needed in an industrial setting, nor do they generate the rate of doubling needed to make the practice a highly efficient industrial procedure.

SUMMARY OF THE INVENTION

Disclosed herein is the discovery that drastic improvements in treatment delivery occur when plants are centrifuged after being contacted, submerged, unsubmerged, soaked, etc. in a solution containing a plant treatment agent. In one embodiment, haploid plants contacted with a colchicine solution are centrifuged to reveal improved chromosomal doubling rates as compared to control plants.

Certain embodiments are drawn to a method for delivering a plant treatment agent to a plant tissue where at least 1% of the surface of a plant is contacted with a solution that comprises the plant treatment agent. A centrifugal force is then applied to the plant. In certain embodiments of the method, the plant is a germinated plant. In certain embodiments of the method, the plant is a corn plant. In certain embodiments of the method, the plant tissue is a meristem, for example, a shoot apical meristem (SAM). In certain embodiments of the method, the plant is within the seed or germinating or at or between the VE, V1, V2, V3, V4, V5, or V6 vegetative growth stages. In certain embodiments of the method, the plant is a haploid corn plant and the plant treatment agent is a chromosome doubling agent, for example, the doubling agent is colchicine. In certain embodiments of the method, the centrifugal force that is applied to the plant is from about 10 g to about 4000 g. In certain embodiments of the method, the time duration of the centrifugal force applied is from about 30 seconds to about 180 minutes. In order to, for example, minimize the potential toxic effects of certain plant treatment agents, in certain embodiments of the method the plant is contacted with the solution comprising the plant treatment agent for less than about 1 hour in duration before the application of the centrifugal force. In certain embodiments of the method, at least 10% of the surface of the plant is contacted with the solution comprising the plant treatment agent before the application of the centrifugal force. In certain embodiments of the invention, at least 80% of the surface of the plant is contacted with the solution comprising the plant treatment agent before the application of the centrifugal force.

Certain embodiments are drawn to a method for delivering a plant treatment agent to a plant tissue where the plant remains in contact with a minimum amount of a plant treatment solution during the application of a centrifugal force. The method comprises first contacting at least 1% of the surface of a plant with a solution comprising the plant treatment agent. A centrifugal force is then applied to the plant, wherein at least 1% of the surface of the plant is contacted with the solution comprising the plant treatment agent during application of the centrifugal force. In certain embodiments of the method, the plant is a germinated plant. In certain embodiments of the method, the plant is a corn plant. In certain embodiments of the method, the plant tissue is a meristem, for example, a shoot apical meristem. In certain embodiments of the method, the plant is within the seed or germinating or at or between the VE, V1, V2, V3, V4, V5, or V6 vegetative growth stages. In certain embodiments of the method, the plant is a haploid corn plant and the plant treatment agent is a chromosome doubling agent, for example, the doubling agent is colchicine. In certain embodiments of the methods, the centrifugal force that is applied to the plant is from about 10 g to about 4000 g. In certain embodiments of the method, the time duration of the centrifugal force applied is from about 30 seconds to about 180 minutes. In order to, for example, minimize the potential toxic effects of certain plant treatment agents, in certain embodiments of the method the plant is contacted with the solution comprising the plant treatment agent for less than about 1 hour in duration before the application of the centrifugal force. In certain embodiments of the method, at least 10% of the surface of the plant is contacted with the solution comprising the plant treatment agent during application of the centrifugal force. In certain embodiments of the method at least 80% of the surface of the plant is contacted with the solution comprising the plant treatment agent during application of the centrifugal force. In certain embodiments of the method, substantially all of the solution comprising the plant treatment agent is removed from contacting the surface of the plant after the application of the centrifugal force. In certain embodiments of the method, the solution comprising the plant treatment agent is contacted with the plant for less than about 4 hours in duration before removal of the plant treatment agent.

Certain embodiments are drawn to a method for delivering a plant treatment agent to a plant tissue, the method comprising two separate applications of a centrifugal force. The method first comprises first contacting at least 1% of the surface of a plant with a solution comprising the plant treatment agent. A centrifugal force is then applied to the plant, wherein at least 1% of the surface of the plant is contacted with the solution comprising the plant treatment agent during application of the centrifugal force. Following the application of the centrifugal force, the centrifugal force is removed. A subsequent centrifugal force is then applied wherein at least a portion of, or a majority of, or significantly all of the plant treatment solution contacting the plant may be removed before or during the application of the subsequent centrifugal force. In certain embodiments of the method, the plant is a germinated plant. In certain embodiments of the method, the plant is a corn plant. In certain embodiments of the method, the plant tissue is a meristem, for example, is a shoot apical meristem. In certain embodiments of the method, the plant is within the seed or germinating or at or between the VE, V1, V2, V3, V4, V5, or V6 vegetative growth stage. In certain embodiments of the method, the plant is a haploid corn plant and the plant treatment agent is a chromosome doubling agent, for example, the doubling agent is colchicine. In certain embodiment of the method, either the first, subsequent, or both of the centrifugal forces applied are from about 10 g to about 4000 g. In certain embodiments of the method, at least 10% of the surface of the plant is contacted with the solution comprising the plant treatment agent prior to the application of the first centrifugal force. In certain embodiments of the method, at least 80% of the surface of the plant is contacted with the solution comprising the plant treatment agent prior to the application of the first centrifugal force. In certain embodiments of the method, at least 10% of the surface of the plant is contacted with the solution comprising the plant treatment agent during application of the first centrifugal force. In certain embodiments of the method, at least 80% of the surface of the plant is contacted with the solution comprising the plant treatment agent during application of the first centrifugal force. As noted, following the application of the first centrifugal force and removal of the first centrifugal force, some portion of, including substantially all or more of, the solution comprising the plant treatment agent may be removed before application of the second (subsequent) application of centrifugal force. In certain embodiments of the method, the solution comprising the plant treatment agent is contacted with the plant for less than about 1 hour in duration before removal of the plant treatment agent.

Certain embodiments provide methods of delivering a plant treatment agent to a selected tissue of a plant, wherein the plant has a surface and the selected tissue is located at, and/or beneath, a portion of plant surface. Such methods comprise applying a centrifugal force to the plant to transport, migrate, push, and the like, a solution that comprises the plant treatment agent to the selected tissue. In certain embodiments, the force pushes or forces the solution into the selected plant tissue. In certain embodiments, the force pushes or forces the solution into cells of the selected tissue. In certain embodiments, at least 5% of the surface of the plant has been contacted with the solution that comprises the plant treatment agent, including plant tissue other than the selected tissue. In certain embodiments, the plant is germinated. In certain embodiments, the selected tissue remains in contact with solution comprising the plant treatment agent that is not absorbed by the plant during at least a portion of the application of the centrifugal force. In certain embodiments, at least 5% of the plant surface remains in contact with the solution during the application of the centrifugal force. In certain embodiments where at least the selected tissue remains in contact with the solution during the application of the centrifugal force, a centrifugal force applied is applied of from about 10 g to about 500 g. In certain embodiments, the selected tissue is maintained in contact with the solution comprising the plant treatment agent that is not absorbed by the plant during the application of the centrifugal force by a plant centrifugation support, during at least a portion of the application of the centrifugal force. In certain embodiments, the selected tissue is separated from the plant treatment agent not absorbed by the plant during at least a portion of the application of the centrifugal force. In certain embodiments where the selected tissue is separated from the treatment agent, a centrifugal force is applied of from about 10 g to about 4000 g, such as from about 500 g to about 2000 g, 2500 g, 3000 g, 3500 g, or 4000 g. In certain embodiments, the selected tissue is maintained separated from the plant treatment agent not absorbed by the plant during the application of the centrifugal force by a plant centrifugation support, during at least a portion of the application of the centrifugal force. In certain embodiments, the plant has an axis that is aligned with the direction of the centrifugal force during at least a portion of the application of the centrifugal force. In certain embodiments, the axis is aligned with the direction of the centrifugal force during the entire application of the centrifugal force. In certain embodiments, the axis of the plant is maintained in alignment with the direction of the centrifugal force by a plant centrifugation support during at least a portion of the application of the centrifugal force. In certain embodiments, the plant contacts the plant centrifugation support and in other embodiments, the plant does not contact plant centrifugation support.

Certain embodiments provide for methods for delivering a plant treatment agent to a selected plant tissue, wherein the plant has a surface and the selected tissue is located at, and/or beneath, a portion of the plant surface. Such methods comprise applying a centrifugal force to the plant to transport, migrate, push, and the like, a solution that comprises the plant treatment agent to the selected tissue, wherein the plant has been contacted with the solution that comprises the plant treatment agent, including plant tissue other than the selected tissue, and wherein the axis of the plant is aligned by a plant centrifugation support during at least a portion of the application of the centrifugal force. In certain embodiments, the force pushes or forces the solution into the selected plant tissue. In certain embodiments, the force pushes or forces the solution into cells of the selected tissue. In certain embodiments, the plant is germinated. In certain embodiments, the plant centrifugation support maintains alignment of the axis of the plant with the direction of the centrifugal force. In certain embodiments, the plant contacts the plant centrifugation support and in other embodiments, the plant does not contact the plant centrifugation support. In certain embodiments, a centrifugal force of from about 10 g to about 4000 g is applied, such as from about 10 g to about 500 g or from about 500 g to about 2000 g, 2500 g, 3000 g, 3500 g, or 4000 g. In certain embodiments, the centrifugal force increases contact of the chromosome doubling agent with the shoot meristem relative to the contact with the chromosome doubling agent achieved without centrifugation. In certain embodiments, the plant is contacted with the solution comprising the chromosome doubling agent for less than about 3 hours or less than about 1 hour in duration before the application of the centrifugal force.

Certain embodiments provide for methods of creating a doubled-haploid corn plant by delivering a chromosome doubling agent to a shoot apical meristem tissue. Such methods comprises applying a centrifugal force to a haploid plant, e.g a $DH_0$ mother plant, to transport, migrate, push, and the like, a solution that comprises the chromosome doubling agent to the shoot apical meristem, wherein the haploid plant has been contacted with the solution that comprises the chromosome doubling agent, including plant tissue other than the shoot apical meristem. In certain embodiments, the force pushes or forces the chromosome doubling agent into the tissue of the shoot apical meristem. In certain embodiments, the forces or pushes the chromosome doubling agent into cells of shoot apical meristem. In certain embodiments, the doubling efficiency resulting from the delivery of the chromosome doubling agent is increased in comparison to delivering the chromosome doubling agent to the shoot apical meristem by only contact of the solution that comprises the chromosome doubling and without application of the centrifugal force. In certain embodiments, the plant is germinated. In certain embodiments, the shoot apical meristem remains in contact with the solution comprising the chromosome doubling agent that is not absorbed by the plant during at least a portion of the application of the centrifugal force. In certain embodiments, at least 5% of the plant surface remains in contact with the solution during the application of the centrifugal force. In certain embodiments, the centrifugal force applied is from about 10 g to about 500 g. In certain embodiments, the shoot apical meristem is maintained in contact with the solution comprising the chromosome doubling agent that is not absorbed by the plant during the application of the centrifugal force by a plant centrifugation support, during at least a portion of the application of the centrifugal force. In certain embodiments, the shoot apical meristem tissue is separated from the solution comprising the chromosome doubling agent not absorbed by the plant during at least a portion of the application of the centrifugal force. In certain embodiments, the centrifugal force applied is from about 10 g to about 4000 g, for example from about 500 g to about 2000, 2500 g, 3000 g, 3500 g, or 4000 g. In certain embodiments, the shoot apical meristem is maintained separated from the chromosome doubling agent not absorbed by the plant during the application of the centrifugal force by a plant centrifugation support, during at least a portion of the application of the centrifugal force. In certain embodiments, the plant has an axis that is aligned with the direction of the centrifugal force during at least a portion of the application of the centrifugal force. In certain embodiments, the axis is aligned with the direction of the centrifugal force during the entire application of the centrifugal force. In certain embodiments, the axis of the plant is maintained in alignment with the direction of the centrifugal force by a plant centrifugation support during at least a portion of the application of the centrifugal force. In certain embodiments, the plant contacts the plant centrifugation support and in certain embodiments, the plant does not contact the plant centrifugation support. In certain embodiments, the centrifugal force increases contact of the chromosome doubling agent with the shoot apical meristem relative to the contact with the chromosome doubling agent achieved without centrifugation. In certain embodiments, the plant is contacted with the solution comprising the chromosome doubling agent for less than about 3 hours or for less than 1 hour in duration before the application of the centrifugal force.

Certain embodiments provide methods for delivering a plant treatment agent to a selected plant tissue, the method comprising the steps of: (a) contacting the surface of a plant with a solution comprising the plant treatment agent, wherein the plant has germinated; (b) applying a centrifugal force to the plant in step (a) contacted with the solution; (c) following the application of the centrifugal force in step (b), removing the plants from centrifugal force and treatment solution; and (d) applying a subsequent centrifugal force to the plant subjected to the centrifugal force in step (b), thereby delivering the plant treatment agent to the plant tissue.

Certain embodiments provide methods for creating a doubled-haploid corn plant from a haploid plant comprising: (a) contacting the haploid plant with a solution comprising a chromosome doubling agent; (b) applying a centrifugal force to the contacted haploid plant of step (a), wherein the centrifugal force causes at least a portion of the solution comprising the chromosome doubling agent to contact at least one cell of a shoot meristem of the haploid plant and wherein a haploid egg is formed from the at least once cell of the shoot meristem, thereby creating a doubled-haploid corn plant.

BRIEF DESCRIPTION OF THE DRAWINGS

FIG. 2 shows a summary of the corn growth and development stages described by Abendroth, et al. 2011 and referred to herein.

FIG. 3 shows a comparison of corn staging systems. *Not applicable. The Horizontal Leaf method is difficult to convert to the Leaf Collar method at V1 and especially in later vegetative stages because of the vertical orientation of the upper leaves at V1 The values for Hortizontal Leaf method relative to the Leaf Collar method are different than published by the USDA-FCIC. **Not applicable. The Leaf Tip method is difficult to correlate to the Leaf Collar method after V14.

DETAILED DESCRIPTION

Figure 1:
FIG. 1 shows exemplary results of aided delivery of plant treatment agents. Two different concentrations of uniconazole were delivered to the shoot apical meristem of several seedlings as shown in comparison to control plants.

It is to be noted that the term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. Unless otherwise specified, units, prefixes, and symbols are denoted in their Système International de Unites (SI) accepted form. Numeric ranges are inclusive of the numbers defining the range.

The headings provided herein are not limitations of the various aspects or aspects of the disclosure, which can be had by reference to the specification as a whole.

Overview

Provided herein are exemplary methods of delivering a plant treatment agent to a tissue of a plant, wherein the plant is contacted on at least a portion of its surface with a plant treatment agent and a centrifugal force is applied to aid in delivery of the plant treatment agent to the plant tissue.

In certain embodiments for delivering a plant treatment agent to a plant tissue, at least a portion of the surface of a plant is contacted with a solution comprising a plant treatment agent. A centrifugal force is then applied to the plant. The plant may be washed if desired, such as with water, either before or after the application of the centrifugal force to wash away excess plant treatment agent. Following treatment, plants can be recovered, transplanted, and grown in a field or a protected environment using standard methods.

Useful Plant Treatment Agents

In the various embodiments provided herein, a plant can be contacted with a wide variety of "plant treatment agents." Thus, as used herein, a "plant treatment agent", or "treatment agent", or "agent" can refer to any exogenously provided compound that can be introduced to the surface of a plant and migrate into a plant tissue. In some embodiments, the plant treatment agent acts extracellularly within the plant tissue, such as interacting with receptors on the outer cell surface. In some embodiments, the plant treatment agent enters into cells within the tissue. In some embodiments, the plant treatment agent is contained within a liquid. Such liquids include, but are not limited to, solutions, suspensions, emulsions, and colloidal dispersions.

In some embodiments, liquids used herein will be of an aqueous nature. However, in certain embodiments, such aqueous liquids that comprise water can also comprise water insoluble components, can comprise an insoluble component that is made soluble in water by addition of a surfactant, or can comprise any combination of soluble components and surfactants.

A "plant treatment solution" or "treatment solution" can refer to any solution of liquid that comprises a plant treatment agent. In certain embodiments, a plant treatment solution comprises a plant treatment agent and the two terms can often be used synonymously. For example, delivering a plant treatment solution comprising the plant treatment agent colchicine to a plant meristem is essentially synonymous with delivering a plant treatment agent comprising colchicine to a plant meristem.

Plant treatment agents include, but are not limited to, macromolecules including polynucleotides including nucleic acids (e.g. DNA and/or RNA), polypeptides, polysaccharides, polyketides, and the like. Polynucleotides can be single-stranded or double-stranded and can include antisense molecules and interfering RNAs. Polynucleotides can include mutations and/or various other modifications, such as to their backbones, that are well known in the art. Polynucleotides include "genetic elements", which comprise recombinant DNA constructs (commonly referred to as "transgenes") that have been inserted into a plant genome, or a nucleotide sequence, or a genetic locus of a plant genome. Thus, in certain embodiments, a user of this invention can deliver a sequence of DNA or RNA to a targeted tissue to alter the expression or inheritance of a plant trait, for example, to effectively "transform" a plant by inserting a genetic element into its genome.

In certain embodiments, a plant treatment agent comprises a plant growth regulator (PGR). PGRs are a class of compounds that affect the cellular processes, growth, development or behavior of a plant or plant part. In some embodiments a PGR is responsible for accelerating or retarding the rate of growth or maturation or otherwise altering the behavior of a plant or plant part. In some embodiments, a PGR is a naturally-occurring plant hormone. In some embodiments, a PGR is a chemical that causes similar effects to that of at least one plant hormone, which induces, among other things, flowering, internode length, apical dominance, ripening, roots to form certain architecture, fruit to set at certain times, flowering to occur including any substance that affects plant growth, development, behavior, or reproduction.

As used herein, uniconazole is (e)-(+/−)-beta-((4-chlorophenyl)methylene)-alpha-(1,1-dimethylethyl)-1h-1,2,4-triazole-1-ethanol, also written as $C_{15}H_{18}CIN_3O$, also known as uniconazole-P. It is a triazole-type plant growth retardant and known antagonist of the plant hormone giberellin that reduces internodal growth.

As used herein, PBZ is paclobutrazol, (2S,3S)-1-(4-chlorophenyl)-4,4-dimethyl-2-(1,2,4-triazol-1-yl) pentan-3-ol, also written as $C_{15}H_{10}CIN_{30}$, a plant growth regulator and triazole fungicide. It is a known antagonist of the plant hormone gibberellins that inhibits giberellin biosynthesis, reducing internodal growth and increasing stem girth. BAP is 6-Benzylaminopurine, N-(Phenylmethyl)-7H-pruin-6-amine, also written as $C_{12}H_{11}N_5$. IAA is indole-3-acetic acid, and IBA is inodole-3-butyric acid. Both are naturally-occurring forms of a class of plant hormones called auxins. Other variations of auxin can be used with this invention, including synthetic auxins, such as 2,4-D (2,4-Dichlorophenoxyactic acid) and 1-NAA (1-Naphthalene acetic acid).

In certain embodiments, macromolecule plant treatment agents are molecules of less than about 10 kD, 5 kD, 4 kD, 2 kD, or 1 kD in molecular weight. In certain embodiments, macromolecule plant treatment agents are molecules of more than 10 kD in molecular weight. Plant treatment agents can also comprise various mono-saccharides and di-saccharides, including, but not limited to, glucose and sucrose.

Plant treatment agents can also comprise various phytohormones, phytohormone agonists, phytohormone antagonists, or agents that stimulate or inhibit phytohormone perception, signaling or synthesis. Plant treatment agents also comprise auxins (e.g. IAA) and auxin inhibitors, cytokinins (e.g. BAP) and cytokinin inhibitors, compounds that can stimulate ethylene production (i.e. ACC and the like) and compounds that can inhibit ethylene production (AVG and the like), and compounds that inhibit ethylene perception (silver and the like). Plant treatment agents also comprise compounds that modulate plant perception, signaling, and/or behavior, such as giberrellins and their inhibitors (e.g. Paclobutrazol (PBZ) or uniconazole), abscisic acid and its inhibitors, and jasmonic acid and its inhibitors. Other examples include peptide hormones, for example, systemin, phytosulfokine, rapid alkalinization factor and the like.

Polynucleotide plant treatment agents such as but not limited to those that function as phytohormone agonists, phytohormone antagonists, or agents that stimulate or inhibit phytohormone movement, perception or synthesis and/or influence other gene regulatory functions, are also contemplated herein.

Plant treatment agents thus include, but are not limited to, various polynucleotides that inhibit expression of genes involved in phytohormone perception or synthesis. In certain embodiments, plant treatment agents comprising any of the aforementioned can be used in conjunction with other plant treatment agents. For example, plant treatment agents comprising any of the aforementioned phytohormones, phytohormone agonists, phytohormone antagonists, nucleic acids, or agents that stimulate or inhibit phytohormone movement, perception or synthesis, whether directly or indirectly, can be used in combination with chromosome doubling agents and this invention.

As used herein, the phrase "chromosome doubling agent" refers to any agent that can cause a cell to contain a duplicated set of chromosomes. In certain embodiments, a chromosome doubling agent is colchicine. In certain embodiments, more than one doubling agent delivered to a targeted or selected tissue through use of this invention, whether simultaneously or in series.

When referring to a tissue of a plant herein, the terms "targeted" and "selected" can be used interchangeably. For example, a target or targeted tissue is synonymous with a selected tissue. A target tissue can be any cell or tissue that a user desires to treat with a plant treatment agent, e.g. the shoot apical meristem.

In certain embodiments, plant treatment agents are water soluble agents. In certain embodiments, however, the use of plant treatment agents with high, intermediate, low or negligible water solubility can be facilitated by the use of liquid compositions that comprise various transfer or conditioning agents. Transfer or conditioning agents can comprise any agent that facilitates migration of plant treatment agents into plant tissues and/or that facilitates uptake of plant treatment agents by the plant. Transfer or conditioning agents include, but are not limited to, (a) surfactants, (b) an organic solvents or an aqueous solutions or aqueous mixtures of organic solvents, (c) oxidizing agents, (d) acids, (e) bases, (f) oils, (g) enzymes, or combinations thereof. In certain embodiments, use of transfer or conditioning agents includes any of an incubation step, a neutralization step (e. g., to neutralize an acid, base, or oxidizing agent, or to inactivate an enzyme), a rinsing step, a rest or recovery step, or combinations thereof whereby the liquid and plant treatment agent contained therein are treated either before, during, or after delivery to the plant tissue. Transfer or conditioning agents thus include, but are not limited to, emulsions, reverse emulsions, liposomes, and other micellar-like compositions. Transfer or conditioning agents include adjuvants, surfactants, and effective molecules contained therein, which include sodium or lithium salts of fatty acids (such as tallow or tallow amines or phospholipids). Transfer or conditioning agents can comprise salts including, but not limited to, sodium, ammonium, calcium, potassium, lithium, magnesium, chloride, sulfide, and sulfate salts. In certain embodiments of the methods, use of counter-ions or other molecules that are known to associate with plant treatment agents is provided. For certain negatively charged plant treatment agents such as polynucleotides, cations such as inorganic ammonium ions, alkyl ammonium ions, lithium ions, polyamines such as spermine, spermidine, or putrescine, and the like can be used. Organic solvents useful in conditioning a plant cell to permeation with certain plant treatment agents including, but not limited to polynucleotides, are solvents such as DMSO, DMF, pyridine, N-pyrrolidine, hexamethyiphosphoramide, acetonitrile, dioxane, polypropylene glycol, or other solvents that are miscible with water. Naturally derived or synthetic oils with or without surfactants or emulsifiers can be used, e. g., plant-sourced oils, crop oils (such as those listed in the 9th Compendium of Herbicide Adjuvants, publicly available on the world wide web (internet) at herbicide.adjuvants.com) can be used. Oils useful in certain liquid compositions used in the methods provided herein include, but are not limited to, paraffinic oils, polyol fatty acid esters, or oils with short-chain molecules modified with amides or polyamines such as polyethyleneimine or N-pyrrolidine.

A "solution comprising a plant treatment agent" as used herein encompasses all manner of solutions that contain a plant treatment agent. Non-limiting examples include solutions comprising colchicine and/or uniconazole and/or amiprophos-methyl (APM). In certain embodiments, the solution comprising a plant treatment agent comprises for example colchicine.

In certain embodiments, a plant treatment agent is a chromosomal doubling agent. Such chromosome doubling agents can enable doubled haploid plant production when used by the methods provided herein. Chromosomal doubling agents can comprise various mitotic inhibitors that cause chromosome doubling. In certain embodiments, the chromosome doubling agent can be a compound such as colchicine, amiprophos methyl, trifluralin, oryzalin, pronamide, or chloropropham.

In certain embodiments, the chromosome doubling agent can be a low mammalian toxicity chromosomal doubling agent. Low mammalian toxicity chromosome doubling agents that can be used in various embodiments provided herein include, but are not limited to, compounds such as: i) 1,2,3-trimethoxy-4-((1S,6R)-6-nitro-cyclohex-3-enyl)-benzene and other related compounds disclosed in US Patent Application Publication 2010/0169999; and ii) compounds disclosed in U.S. Pat. No. 5,866,513 to Michelotti et al. The compounds disclosed in U.S. Patent Application Publication 2010/0169999 and in U.S. Pat. No. 5,866,513 are incorporated herein by reference. In particular, 76 compounds disclosed in Table I and 1a on Cols. 3-4, 5-6, and 7-8 of U.S. Pat. No. 5,866,513 are each incorporated herein by reference. In certain embodiments, the chromosome doubling agent comprises a polynucleotide.

In certain embodiments the solution comprising a plant treatment agent comprises colchicine in an amount as high as about 4000 parts per million (ppm) of colchicine in the solution. In certain embodiments, the colchicine concentration is in an amount as low as about 50 ppm of colchicine in the solution. In certain embodiments, the colchicine concentration is in an amount of from about 50 ppm to about 4000 ppm of colchicine in the solution. In certain embodiments, the colchicine is in an amount of from about 50 ppm to about 2500 ppm, or from about 50 ppm to about 1000 ppm, or from about 50 ppm to about 1500 ppm, or from about 50 ppm to about 1000 ppm, or from about 50 ppm to about 500 ppm, or from about 50 ppm to about 250 ppm, or from about 50 ppm to about 100 ppm of colchicine in the solution. In certain embodiments, the colchicine is in an amount of from about 100 ppm to about 4000 ppm, or from about 250 ppm to about 4000 ppm, or from about 500 ppm to about 4000 ppm, or from about 1000 ppm to about 4000 ppm, or from about 1000 ppm to about 4000 ppm, or from about 2500 ppm to about 4000 ppm of colchicine in the solution. In certain embodiments, the colchicine is in an amount of from about 1100 ppm to about 1500 ppm of colchicine in the solution. In certain embodiments, the colchicine is in an amount of from about 300 ppm to about 3000 ppm.

It is important to note that these methods can be used in conjunction with any concentration of a plant treatment agent suggested or known in the art to be useful for treating plants.

To reduce plant stress and mortality due to handling, centrifugation, or infection, plants can be treated with additional hormones, salts, antibiotics and other pesticides in conjunction with the methods described herein, either before, during, between, or after centrifugation steps. These additional treatments can prevent infection while the plants recovering, or affect plant growth in a way that improves survival. Example 5 shows how plant growth regulators in a treatment solution be delivered to plant tissues to affect plant development in a way that improves the ability of a plant to survive handling, transport, and transplanting following the application of a centrifugal force.

Contacting Plants with Treatment Agents

Contact between a plant and a treatment solution can occur before, during, or after the application of a centrifugal force. In certain embodiments, contact between the plant surface and the treatment agent is achieved by dipping, submerging, or otherwise inserting the plant into a reservoir of liquid comprising the plant treatment agent. Other methods of contacting at least a portion of the surface of a plant with a plant treatment agent include spraying or misting a plant with a solution comprising a plant treatment agent or agitating or tumbling a plant in a solution comprising a plant treatment agent. In certain embodiments, contact between the plant surface and the treatment agent is achieved by placing a plant in a container and then adding treatment solution to the container with the plant. The treatment agent can then be decanted or otherwise drained from the container while the plant remains within, if, for example, a user desires to perform a serial centrifugation, or the plant can be removed from the container before or during removal of the treatment agent.

In certain embodiments, at least 1%, 2%, 3%, 4%, 5%, 6%, 7%, 8%, 9%, 10%, 15%, 20%, 25%, 30%, 40%, 50%, 60%, 70%, 80%, 90%, 95%, 99%, or 100% of the surface of the plant is in contact with the solution comprising the plant treatment agent prior to the application of a centrifugal force. In certain embodiments, at least 3%, 4%, 5%, 6%, 7%, 8%, 9%, 10%, 15%, 20%, 25%, 30%, 40%, 50%, 60%, 70%, 80%, 90%, 95%, 99%, or 100% of the surface of the plant is in contact with the solution comprising the plant treatment agent when the application of the centrifugal force begins.

As used herein, a macro-scale plant treatment refers to contacting more than a miniscule area of the plant surface with the solution comprising the plant treatment agent. For example, in certain embodiments, a macro-scale treated plant is one in which at least 3%, 4%, 5%, 6%, 7%, 8%, 9%, 10%, 15%, 20%, 25%, 30%, 40%, 50%, 60%, 70%, 80%, 90%, 95%, 99%, or 100% of the surface of the plant has been contacted with the solution comprising the plant treatment agent prior to the application of a centrifugal force. In certain embodiments, at least a portion of the plant surface that is contacted with the solution includes plant tissue other than a selected plant tissue. In certain embodiments, the selected plant tissue is not part of the surface of the plant that is contacted with the solution. Thus, in certain embodiments, during application of the centrifugal force, at least a portion of the solution comprising the plant treatment agent migrates or travels under the influence of the centrifugal force to the selected plant tissue.

In certain embodiments, at least a portion of the surface of the plant remains in contact with the solution comprising the plant treatment agent for at least a majority of the duration of the application of the centrifugal force, at least a portion of the surface of the plant remains in contact with the solution comprising the plant treatment agent for substantially the entire duration of the application of the centrifugal force, and/or at least a portion of the surface of the plant remains in contact with the solution comprising the plant treatment agent for the entire duration of the application of the centrifugal force. In certain embodiments, at least a portion of the surface of the plant remains in contact with the solution comprising the plant treatment agent for at least about 25%, 50%, 75%, 80%, 85%, 90%, 95%, 98%, 99%, or 100% of the duration of the application of the centrifugal force. In certain embodiments, the amount of plant surface that remains in contact with the solution comprising the plant treatment agent during at least a portion of the application of the centrifugal force is at least about 1%, 2%, 3%, 4%, 5%, 6%, 7%, 8%, 9%, 10%, 15%, 20%, 25%, 30%, 40%, 50%, 60%, 70%, 80%, 90%, 95%, 99%, or 100% of the surface of the plant. In certain embodiments, regardless of the percentage of the surface of the plant that remains in contact with the solution, the selected tissue remains submerged within the solution. For example, wherein the shoot apical meristem of a corn plant is submerged in the solution but portions of the leaves are not. In certain embodiments, regardless of the percentage of the surface that remains in contact with the solution, the surface of the selected tissue is free or becomes free during the application of the centrifugal force of the solution. For example, wherein the surface of the shoot apical meristem of a corn plant is free of solution but the roots remain submerged. It is understood that whereas the surface of the selected tissue is "free" of the solution, trace amounts of solution and/or the plant treatment agent can still be present in the selected tissue.

In certain embodiments, all or substantially all of the solution comprising a plant treatment agent is removed from the surface of the plant during centrifugation and/or none or substantially none of the solution remains on the plant surface after removal of the centrifugal force. In certain embodiments, greater than about 95%, 96%, 97%, 98%, or 99% of the plant surface is free of the solution after removal of the centrifugal force without needing an additional step of solution removal, i.e., less than about 5%, 4%, 3%, 2%, or 1% of the plant surface remains in contact with the solution comprising the plant treatment agent by the end of the application of the centrifugal force without needing an additional step of solution removal.

As used herein, a "contacting step" is any process wherein a plant part is brought into contact with a solution comprising a plant treatment agent. A wide range of durations is possible for the contacting step, especially considering how the contacting step is type of incubation period and embodiments described herein provide for a wide range of incubation durations useful with this invention.

Depending on a number of variables, and not limited to the germplasm under study, the activity or concentration of plant treatment agent used, the location of the targeted tissue, the speed of centrifugation, or a combination of these and other variables, the duration of time between when the plant surface is contacted with the solution comprising the plant treatment agent and the application of the centrifugal force, as described elsewhere herein, can be as short as the minimum necessary to ensure that at least some of the plant treatment agent reaches the targeted tissue during a subsequent centrifugation. In certain embodiments, a user briefly dips the plant into a solution comprising a plant treatment agent just long enough to cover the selected tissue that the user is targeting, to cover tissues not being targeted, for example tissues that surround the selected tissue, or both the selected tissues and tissues not being targeted. For example, dipping the shoot tips of a haploid plant into a liquid comprising a doubling agent just long enough to ensure that that the shoot apical meristem and/or the tissues surrounding it are contacted with the doubling agent. This could be as little as about one second, possibly even less, with an upper limit depending on a number of factors, including the effects (e.g. toxicity) of the agent on the plants and how long the plants can survive under such conditions.

In certain embodiments, a particular germplasm can be treated with a non-toxic agent, or a low concentration of treatment agent, by soaking plants for several days or perhaps even a few weeks, provided measures are taken to ensure the plants survive the treatment and the user is willing to accept whatever additional effects such a prolonged exposure to the agent has on the plants.

Useful Types of Plants

Unless otherwise specified, this disclosure is not limited to any particular type of plant. For example, the plant may be a commercial commodity crop or an ornamental plant. For example, in certain embodiments, the plant is a monocot plant or is a member of the family Poaceae, wheat plant, maize plant, sweet corn plant, rice plant, wild rice plant, barley plant, rye, millet plant, sorghum plant, sugar cane plant, turfgrass plant, bamboo plant, oat plant, brome-grass plant, *Miscanthus* plant, pampas grass plant, switchgrass (*Panicum*) plant, and/or teosinte plant, or is a member of the family Alliaceae, onion plant, leek plant, garlic plant; or wherein the plant is a dicot plant or is a member of the family Amaranthaceae, spinach plant, *quinoa* plant, a member of the family Anacardiaceae, mango plant, a member of the family Asteraceae, sunflower plant, endive plant, lettuce plant, artichoke plant, a member of the family Brassicaceae, *Arabidopsis thaliana* plant, rape plant, oilseed rape plant, broccoli plant, Brussels sprouts plant, cabbage plant, canola plant, cauliflower plant, kohlrabi plant, turnip plant, radish plant, a member of the family Bromeliaceae, pineapple plant, a member of the family Caricaceae, *papaya* plant, a member of the family Chenopodiaceae, beet plant, a member of the family Curcurbitaceae, melon plant, cantaloupe plant, squash plant, watermelon plant, honeydew plant, cucumber plant, pumpkin plant, a member of the family Dioscoreaceae, yam plant, a member of the family Ericaceae, blueberry plant, a member of the family Euphorbiaceae, cassava plant, a member of the family Fabaceae, alfalfa plant, clover plant, peanut plant, a member of the family Grossulariaceae, currant plant, a member of the family Juglandaceae, walnut plant, a member of the family Lamiaceae, mint plant, a member of the family Lauraceae, avocado plant, a member of the family Leguminosae, soybean plant, bean plant, pea plant, a member of the family Malvaceae, cotton plant, a member of the family Marantaceae, arrowroot plant, a member of the family Myrtaceae, guava plant, *eucalyptus* plant, a member of the family Rosaceae, peach plant, apple plant, cherry plant, plum plant, pear plant, prune plant, blackberry plant, raspberry plant, strawberry plant, a member of the family Rubiaceae, coffee plant, a member of the family Rutaceae, citrus plant, orange plant, lemon plant, grapefruit plant, tangerine plant, a member of the family Salicaceae, poplar plant, willow plant, a member of the family Solanaceae, potato plant, sweet potato plant, tomato plant, *Capsicum* plant, tobacco plant, tomatillo plant, eggplant plant, *Atropa belladona* plant, *Datura stramonium* plant, a member of the family Vitaceae, grape plant, a member of the family Umbelliferae, carrot plant, or a member of the family Musaceae, banana plant; or wherein the plant is a member of the family Pinaceae, cedar plant, fir plant, hemlock plant, larch plant, pine plant, spruce plant.

Unless otherwise specified, as used herein, a plant may be any whole plant, or part of a plant, or tissue culture derived from a plant, or plant seed; having a tissue to which a plant treatment agent can be delivered. A plant may be of various chromosomal content, such as haploid, diploid, triploid, tetraploid, etc. Polyploidy refers generally to a condition of having a ploidy level greater than triploid. In certain embodiments, a distinction is made between plant tissues grown in tissue culture and non-tissue culture plants.

Unless otherwise specified, as used herein, the surface of a plant refers to the surface that is generally exposed to the external environment surrounding the plant without pulling, cutting, etc. the plant to expose additional areas. For example, if a plant is submerged completely in a solution, the surface of the plant is generally the portion of the plant that would come in contact with the solution.

A plant tissue can be any plant tissue. In certain embodiments, a plant tissue can include a functional meristem or grouping of cells capable of forming a functional meristem. A functional meristem is defined as a center of pluripotent cells that has the ability to give rise to new plant tissues or organs. In certain embodiments, the plant tissue is a meristem tissue such as a root apical meristem or a shoot apical meristem.

In certain embodiments, a plant treatment agent is delivered to a targeted or selected plant tissue. A plant tissue can be targeted or selected based on the tissue's response to the plant treatment agent and/or the influence over the plants growth, characteristics, genetics, yield, etc., that is sought to be achieved. For example, the shoot apical meristem, particularly of a $DH_0$ plant, can be selected for the delivery of a chromosome doubling agent. The selected tissue can be located at the surface of the plant and/or it can be located beneath the plant surface or beneath a portion of the plant surface. Thus, in certain embodiments, wherein even the entire surface of a plant is contacted by a solution comprising a plant treatment agent such as by completely submerging the plant, at least a portion of the selected tissue may not be contacted by the solution.

A plant for use in methods described herein can be at any of various developmental stages. For example, corn plants can be described by their vegetative growth and reproductive stages, and as used herein, the stages of corn kernel development (Leaf Collar method: V1-Vn, Vt, R1-R6, etc.) are as described in Abendroth, L. J., R. W. Elmore, M. J. Boyer, and S. K. Marlay, 2011, Corn Growth and Development, PMR 1009, Iowa State University Extension, Ames, Iowa (FIGS. 2, 3, 14-83) and summarized in FIG. 2. The choice of developmental stage can depend on many factors such as, but not limited to, the ability of the plant treatment agent to access a certain tissue at a certain developmental stage, the correlation between the need for the plant treatment agent and a certain developmental stage, or the physical size of the plant and the practicality of subjecting it to a centrifugal force. In certain embodiments, the plant is a seed. In certain embodiments, the plant is a germinated plant. In certain embodiments, the plant is a mature plant.

In certain embodiments, prior to germination, the plant or a propagule of the plant is contacted with a plant treatment agent, and subjected to centrifugation in order to deliver the treatment agent to at least one selected tissue of the plant. In certain embodiments, embryo rescue techniques known in the art are used to excise an embryo from the seed prior to germination of the seed in order to better contact the embryo to the treatment agent. After excision, the embryo can be cultured in vitro or otherwise grown in conditions that promote its survival and development into a seedling. Thus, delivery of a plant treatment agent to selected tissues of a plant prior to germination can be improved using a variety of techniques currently known in the art, including embryo rescue techniques, thereby allowing the embryo to be contacted by the plant treatment agent during centrifugation. In certain embodiments, these methods are used to deliver a doubling agent to a meristem of a haploid embryo in order to create at least one doubled haploid reproductive tissue capable of producing functional, haploid gametes.

In certain embodiments, the plant is a corn plant. In certain embodiments, the plant is a corn plant and the plant tissue is a meristem. In certain embodiments, the plant is a corn plant and the plant tissue is a shoot apical meristem (SAM). In certain embodiments, the plant is a corn plant, the plant tissue is a shoot apical meristem, and the corn plant is within the seed or germinating or at or between the VE, V1, V2, V3, V4, V5, or V6 growth stage. In certain embodiments, the plant is a haploid corn plant, the plant tissue is a shoot apical meristem, the corn plant is within the seed or germinating or at or between the VE, V1, V2, V3, V4, V5, or V6 vegetative growth stage, and the plant treatment agent is a chromosome doubling agent, such as colchicine.

Centrifugation

A centrifugal force may be applied in any of various manners but most commonly is achieved using a centrifuge. As used herein, reference to centrifugation is synonymous with the application of a centrifugal force, and the terms "spin" and "centrifugation" are used synonymously herein.

Centrifugal parameters reported here are consistent with the formula $RCF=1.12R(RPM/1000)^2$, wherein RCF=relative centrifugal force, R=the radius of rotation and RPM=the rotational speed measured in revolutions per minute. The magnitude of acceleration represented by RCF can also be represented in multiples of "g" (or "× g"), wherein g represents the standard acceleration of gravity at the Earth's surface. Thus, 50 g or 50×g or 50 RCF represent equivalent acceleration values. The RCF and g values used herein represent the acceleration applied to the sample at or near the bottom of the centrifuge sample ($RCF_{max}$) container once the RPM has reached the speed set by the user. Thus, $RCF=RCF_{max}=1.12R_{max}(RPM_{max}/1000)^2$. It is expected that one of ordinary skill could determine the RCF at any point along the radius of rotation for a given speed. For example, one of ordinary skill might prefer to use the RCF$_{min}$ (the RCF applied to the most proximal end of the centrifuge sample container), or the RCF$_{ave}$ (the average RCF applied across the entire centrifuge sample container) to practice the invention disclosed herein. Embodiments of the invention wherein a centrifugal force is applied to a plant include using any method of acceleration to generate forces that are essentially equivalent in effect to those described herein, regardless of how they are calculated or achieved.

Centrifugations speeds described herein were conducted using a SX4750A swinging-bucket rotor in a Beckman Coulter Allegra X-14 series centrifuge. When a value of 50 RCF (×g) on the Allegra X-14 using a SX4750A rotor was entered into the electronic control panel, it resulted in an R$_{max}$ of approximately 463.5 RPM, which produced an RCF$_{max}$=50 g, an RCF$_{ave}$=34 g, and an RCF$_{min}$=31.3. Entering a value of 10 RCF (×g) resulted in RCF$_{max}$=10, RCF$_{ave}$=14, and R$_{min}$=7.5. Other centrifuge setups could require different parameters to generate approximately the same acceleration, and it is anticipated that users of standard skill in this area can translate these values to other systems or devices operating on similar principals without undue experimentation.

The adjustment of centrifugation parameters to generate good results using different centrifugation setups or devices is considered within the scope of this invention.

In various embodiments of the invention, plants can be treated in any manner that allows an acceleration to be applied to the plant, e.g. via centrifugal force. Generally, a plant is placed in a container that is compatible with being placed in a centrifuge (a centrifuge sample container). In certain embodiments, the container can be a small container, such as a tube, in which a single or a few plants are placed. In certain embodiments, the container can be a large container, such as flask, bottle, box, net or reservoir in which many plants can be centrifuged together simultaneously and/or contacted with a plant treatment agent.

In certain embodiments, plants may be subjected to a centrifugal force while remaining in the same centrifuge container together or they may be separated and divided into other containers, such as placed singly or a few in separate containers for centrifugation. A large number of plants placed singly in separate containers can be centrifuged at once, or they could be centrifuged a few at a time, or individually and sequentially. In some embodiments, more than one plant is treated together in one centrifugation and then the plants are treated singly in separate containers during an additional centrifugation, e.g. as during a double spin and/or as part of a serial centrifugation treatment.

In certain embodiments, it is not necessary to keep the target tissue separate from the reserve treatment agent nor is it necessary to align the target tissue with respect to the force of acceleration generated during the planned centrifugation, for example, during a submerged centrifugation wherein the target tissue is contacted and/or submerged in reserve treatment agent during centrifugation. In certain embodiments wherein the target tissue is in contact or submerged during application of a centrifugal force, some portion of the plant surface is also contacted or submerged in reserve treatment solution during centrifugation.

In certain embodiments it is necessary to prevent the target tissue from contacting and/or submerging into the reserve treatment agent during centrifugation and necessary to align the target tissue with respect to accelerative forces generated during centrifugation, for example, during an unsubmerged centrifugation wherein the target tissue is prevented from becoming submerged and/or contacting the reserve treatment agent and the target tissue is aligned with respect to the force of acceleration generated during centrifugation. Maintaining a certain orientation may be done for a number of reasons, such as to facilitate the movement of the plant treatment agent into a target tissue or region of the plant, or to remove agent from the surface of the plant, or simply to aid in the handling of the plants during steps upstream or downstream of a given centrifugation step.

Useful Centrifugal Forces

In certain embodiments, after at least a portion of the surface of a plant is contacted with a plant treatment agent, a centrifugal force of at least about 10 g is applied to the plant. In certain embodiments, the centrifugal force applied is not greater than about 50 g. In certain embodiments, the centrifugal force applied is from about 10 g to about 50 g. In certain embodiments, the centrifugal force applied is not greater than about 100 g. In certain embodiments, the centrifugal force applied is from about 10 g to about 100 g. In certain embodiments, the centrifugal force applied is not greater than about 250 g. In certain embodiments, the centrifugal force applied is from about 10 g to about 250 g. In certain embodiments, the centrifugal force applied is not greater than about 500 g. In certain embodiments, the centrifugal force applied is from about 10 g to about 500 g. In certain embodiments, the centrifugal force applied is not greater than about 750 g. In certain embodiments, the centrifugal force applied is from about 10 g to about 750 g. In certain embodiments, the centrifugal force applied is not greater than about 1000 g. In certain embodiments, the centrifugal force applied is from about 10 g to about 1000 g. In certain embodiments, the centrifugal force applied is from about 500 g to about 1000 g. In certain embodiments, the centrifugal force applied is not greater than about 1250 g. In certain embodiments, the centrifugal force applied is from about 10 g to about 1250 g. In certain embodiments, the centrifugal force applied is from about 750 g to about 1250 g. In certain mbodiments, the centrifugal force applied is not greater than about 1500 g. In certain embodiments, the centrifugal force applied is from about 10 g to about 1500 g. In certain embodiments, the centrifugal force applied is from about 1000 g to about 1500 g. In certain mbodiments, the centrifugal force applied is not greater than about 1750 g. In certain embodiments, the centrifugal force applied is from about 10 g to about 1750 g. In certain embodiments, the centrifugal force applied is from about 1250 g to about 1750 g. In certain mbodiments, the centrifugal force applied is not greater than about 1000 g. In certain embodiments, the centrifugal force applied is from about 10 g to about 1000 g. In certain embodiments, the centrifugal force applied is from about 1500 g to about 1000 g. In certain embodiments, the centrifugal force applied is not greater than about 2000 g. In certain embodiments, the centrifugal force applied is from about 10 g to about 2000 g. In certain embodiments, the centrifugal force applied is from about 300 g to about 2000 g. In certain embodiments, the centrifugal force applied is not greater than about 2250 g. In certain embodiments, the centrifugal force applied is from about 10 g to about 2250 g. In certain embodiments, the centrifugal force applied is from about 1750 g to about 2250 g. In certain embodiments, the centrifugal force applied is not greater than about 2500 g. In certain embodiments, the centrifugal force applied is from about 10 g to about 2500 g. In certain embodiments, the centrifugal force applied is from about 1000 g to about 2500 g. In certain embodiments, the centrifugal force applied is not greater than about 2750 g. In certain embodiments, the centrifugal force applied is from about 10 g to about 2750 g. In certain embodiments, the centrifugal force applied is from about 2250 g to about 2750 g. In certain mbodiments, the centrifugal force applied is not greater than about 3000 g. In certain embodiments, the centrifugal force applied is from about 10 g to about 3000 g. In certain embodiments, the centrifugal force applied is from about 2500 g to about 3000 g. In certain mbodiments, the centrifugal force applied is not greater than about 3250 g. In certain embodiments, the centrifugal force applied is from about 10 g to about 3250 g. In certain embodiments, the centrifugal force applied is from about 2750 g to about 3250 g. In certain embodiments, the centrifugal force applied is not greater than about 3500 g. In certain embodiments, the centrifugal force applied is from about 10 g to about 3500 g. In certain embodiments, the centrifugal force applied is from about 3000 g to about 3500 g. In certain embodiments, the centrifugal force applied is not greater than about 3750 g. In certain embodiments, the centrifugal force applied is from about 10 g to about 3750 g. In certain embodiments, the centrifugal force applied is from about 3250 g to about 3750 g. In certain embodiments, the centrifugal force applied is not greater than about 4000 g. In certain embodiments, the centrifugal force applied is from about 10 g to about 4000 g. In certain embodiments, the centrifugal force applied is from about 3500 g to about 4000 g.

Useful Centrifugation Durations

In certain embodiments, the centrifugal force is applied for at least about 1 second. In certain embodiments, the centrifugal force is applied for at least about 5 seconds. In certain embodiments, the centrifugal force is applied for at least about 10 seconds. In certain embodiments, the centrifugal force is applied for at least about 15 seconds. In certain embodiments, the centrifugal force is applied for at least about 10 seconds. In certain embodiments, the centrifugal force is applied for at least about 30 seconds. In certain embodiments, the centrifugal force is applied for at least about 40 seconds. In certain embodiments, the centrifugal force is applied for at least about 50 seconds. In certain embodiments, the centrifugal force is applied for at least about 60 seconds. In certain embodiments, the centrifugal force is applied for at least about 90 seconds. In certain embodiments, the centrifugal force is applied for at least about 2 minutes. In certain embodiments, the centrifugal force is applied for at least about 3 minutes. In certain embodiments, the centrifugal force is applied for at least about 5 minutes. In certain embodiments, the centrifugal force is applied for at least about 10 minutes. In certain embodiments, the centrifugal force is applied for at least about 15 minutes. In certain embodiments, the centrifugal force is applied for at least about 10 minutes. In certain embodiments, the centrifugal force is applied for at least about 30 minutes. In certain embodiments, the centrifugal force is applied for at least about 45 minutes. In certain embodiments, the centrifugal force is applied for at least about 60 minutes. In certain embodiments, the centrifugal force is applied for at least about 90 minutes. In certain embodiments, the centrifugal force is applied for at least about 110 minutes. In certain embodiments, the centrifugal force is applied for at least about 150 minutes. In certain embodiments, the centrifugal force is applied for at least about 180 minutes.

In certain embodiments, the centrifugal force is applied for between about 1 second and about 60 minutes or about 10 seconds and about 60 minutes. In certain embodiments, the centrifugal force is applied for between about 1 second and about 45 minutes or about 1 second and about 45 minutes, or for between about 1 second and about 30 minutes or about 1 second and about 30 minutes, or for between about 1 second and about 10 minutes or about 1 second and about 10 minutes, or for between about 1 second and about 15 minutes or about 1 second and about 10 minutes, or for between about 1 second and about 10 minutes, or for between about 1 second and about 5 minutes or about 1 second and about 10 minutes, or for between about 1 second and about 10 minutes or about 1 second and about 10 minutes. In certain embodiments, the centrifugal force is applied for between about 1 second and about 180 minutes.

Useful Incubation Times

Methods of delivering plant treatment agents generally involve exposing the plant to the treatment agent. This can require exposure to the plant treatment agent for an extended period of time in order to permit sufficient migration of the agent into the selected tissues and/or cells of the plant. For a variety of reasons, including potentially toxic side effects of some treatment agents and/or because it is more efficient, it may be desirable to limit the time that the plant is contacted with the plant treatment agent. Certain embodiments comprising the application of a centrifugal force to the plant may shorten the time required for the plant to be contacted with a plant treatment agent to achieve sufficient delivery of the plant treatment agent to a plant tissue, such as to achieve a desired change in the plant or plant tissue.

In certain embodiments, a plant is contacted with the solution comprising a plant treatment agent for less than about 3.5 hours, or less than about 2 hours, or less than about 1 hour, or less than about 45 minutes, or less than about 30 minutes, or less than about 10 minutes, or less than about 10 minutes, or less than about 5 minutes, or less than about 1 minute before the application of a centrifugal force.

Figure 7:
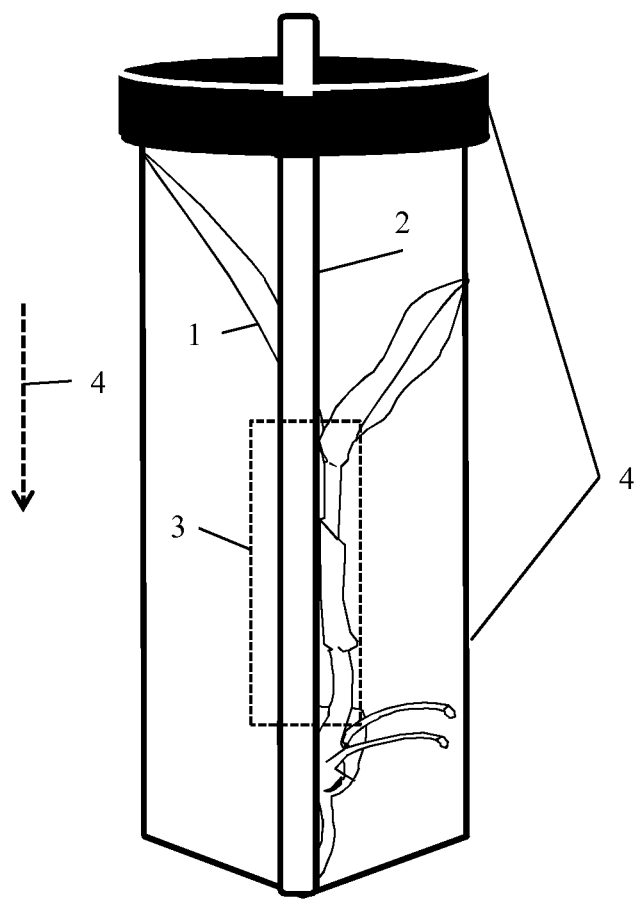
FIG. 7 shows one example of how an individual seeding 1 can be associated with a PCS by being secured to a single PCS 2 and the plant-PCS arrangement placed into a centrifuge container 4. In this case, the centrifuge container 4 is a centrifuge tube with a lid with a hole for the PCS to extend through, but various other types of centrifuge containers will also be useful with this invention. The dashed box 3 represents an area of the plant 1 where plants can be secured to a PCS 2. Other orientations of the plant 1 relative to the force of acceleration 4 can be used when certain other tissues of the plant 1 are targeted.

In certain embodiments, the plant is contacted by the treatment agent for only the amount of time necessary to contact the plant with the agent and load the plant into the centrifuge and begin centrifugation. In certain other embodiments, the plant can remain in a container while a treatment agent is added, and then removed. For example, a plant and PCS (plant centrifuge support) combination, such as shown in FIG. 7, can be used in conjunction with an automated system that forces treatment agent into, or removes treatment agent from, the container while the plant remains inside the container. In certain embodiments, a corn plant can be placed in a centrifuge container and secured by a PCS, such as shown in FIG. 7, wherein a manual or automated system delivers a treatment agent to container up to the point that the selected tissue, or tissues surrounding it, is contacted and/or submerged. In certain embodiments, an automated or manual system further removes the bulk of treatment agent from the container, leaving some treatment agent still on or in the plant, thus preparing the plant for a subsequent unsubmerged centrifugation. In some embodiments, a target tissue is contacted with a liquid doubling agent comprising, for example, colchicine for less than one second before applying a centrifugal force.

In certain embodiments, at least a portion of the surface of a plant can be contacted with a plant treatment agent by placing, submerging, or dipping a plant into a reservoir of liquid comprising a plant treatment agent and then removing the plant from the solution before subjecting the plant to centrifugation. In certain embodiments, a plant treatment agent can be added to a container that contains a plant, and then the plant treatment agent can be removed after a period of time, leaving the plant in the container with some residual treatment agent still in or on the plant. The plant may remain in the solution for less than one second, about one second, or at least about 5 seconds, or at least about 10 seconds, or at least about 30 seconds, or at least about one minute, at least about five minutes, at least about ten minutes, at least about 10 minutes, at least about 30 minutes, at least about 45 minutes, at least about 1 hour, 1.5 hours, 2 hours, 2.5 hours, 3 hours or longer.

In certain embodiments, a haploid plant is contacted with a solution comprising a chromosome doubling agent, such as colchicine, for between about 5 minutes and about 1 hour before the application of a centrifugal force.

Centrifugation Techniques

In certain embodiments, during centrifugation, droplets of treatment agent in contact with the plant surface or otherwise inside the centrifuge container with the plant at the beginning of the centrifugation will be pushed by accelerative forces generated during centrifugation either into the plant or pushed through the centrifuge container until stopped by a wall and/or bottom of the centrifuge container. Once stopped, the solution will begin to collect in the predictable way that liquids do, depending on the shape of the inner surface(s) of the centrifuge container. The volume of treatment agent that is centrifuged with a plant and that collects outside of the plant during application of the centrifugal force is called the "reserve" treatment agent. The volume of treatment agent absorbed into the plant during application of a centrifugal force is called the "absorbed" treatment agent.

In certain embodiments, depending on how plants are oriented during centrifugation and/or how much treatment solution is in the centrifuge container with the plants during centrifugation, either the target tissue, and/or the surface tissues surrounding the target tissue, will be submerged or unsubmerged in the reserve treatment agent during the application of a centrifugation force.

Certain embodiments provide methods for delivering a plant treatment agent to a plant tissue wherein the method comprises contacting at least the surface of a plant with a solution that comprises the plant treatment agent. Unless otherwise stated, all of the parameters disclosed elsewhere herein for contacting a plant with a solution comprising a plant treatment agent and applying a centrifugal force are applicable to such methods. In certain embodiments, the amount of plant surface contacted is at least about 1%, 2%, 3%, 4%, 5%, 6%, 7%, 8%, 9%, 10%, or more. In certain embodiments, the plant has germinated. After contacting the plant, a centrifugal force is applied to the plant which has been contacted with the solution comprising the plant treatment agent. During the application of the centrifugal force, the force will tend to drive the solution in the direction of the force. Depending on the amount of force, duration of the force, and physical characteristics of the plant and the container, at least a portion of the solution attached to the plant prior to the application of the centrifugal force may be removed from the surface of the plant during application of the centrifugal force. However, in some embodiments, an amount of solution sufficient to keep at least a portion of the plant, such as the selected tissue or the tissues surrounding it, contacted and/or submerged, is present. In certain embodiments, at least about 1%, 2%, 3%, 4%, 5%, 6%, 7%, 8%, 9%, 10%, or more of the plant surface remains in contact with the solution during the application of the centrifugal force. In certain embodiments, greater than about 25%, 50%, 75%, 80%, 85%, 90%, 95%, 98%, 99%, or 100% of the solution is removed from contact with the surface of the plant during the centrifugation step. In certain embodiments, a centrifugal force of from about 10 g to about 4000 g, as specified in greater detail elsewhere herein, is applied. In certain embodiments, the axis of the plant is aligned relative to the direction of the centrifugal force during step.

In certain embodiments, the plant is aligned with the direction of the centrifugal force within a certain degree. In certain embodiments, a plant is associated with a plant centrifuge support (PCS), which is described in detail elsewhere herein. A plant associated with a PCS can be centrifuged completely submerged in a solution, substantially submerged in a solution, partially submerged in a solution, or substantially free of solution, wherein the plant is not submerged in the solution (e.g., where the solution contacting the plant is only that which adheres to the surface of the plant after contact with the solution), etc. In certain embodiments, a plant is attached to a PCS such as wrapped to, tied to, bound to, etc. In certain embodiments, the axis of a plant is maintained by a PCS during the application of the centrifugal force. In certain embodiments, the PCS maintains alignment of the axis of the plant with the direction of the centrifugal force within a certain degree. In certain embodiments, the plant is in direct contact with the plant centrifugation support whereas in other embodiments the plant is not in direct contact with the plant centrifugation support. In certain embodiments, the centrifugal force causes migration of the plant treatment agent such that the plant treatment agent contacts a tissue of the plant not contacted when the plant was contacted to the plant treatment agent prior to the application of the centrifugal force. In certain embodiments, the plant tissue is a meristem, such as a shoot apical meristem (SAM). In certain embodiments, the plant is a corn plant, for example a corn plant at the VE, V1, V2, V3, V4, V5, or V6 vegetative growth stage.

Unless otherwise stated, all of the parameters disclosed elsewhere herein for contacting a plant with a solution comprising a plant treatment agent and applying a centrifugal force are applicable to methods involving creating double-haploid plants, increasing doubling efficiency, and the like. Certain embodiments provide for methods of creating a doubled-haploid corn plant. The surface of a haploid plant such as a $DH_0$ mother plant is contacted with a solution comprising a chromosome doubling agent. The amount of surface contacted can be any amount as described in greater detail elsewhere herein. A centrifugal force is then applied to the $DH_0$ mother plant. In certain embodiments, at least a certain amount of doubling efficiency is achieved as evidenced by certain Examples disclosed herein. In addition to creating a doubled-haploid plant, the method can also increase the doubling efficiency achieved over other methods as evidenced by certain Examples disclosed herein. During the creation of a double-haploid plant, the $DH_0$ mother plant produces at least one haploid corn egg, thereby creating a doubled-haploid corn plant. In certain embodiments, at least 5% of the plant surface, or another amount specified in more detail elsewhere herein, remains in contact with the solution comprising the chromosome doubling agent during the application of the centrifugal force. In other embodiments, greater than 99% of the solution comprising the chromosome doubling agent, or another amount specified in more detail elsewhere herein, is removed from contact with the surface of the plant during the application of the centrifugal force. In certain embodiments, a centrifugal force of from about 10 g to about 4000 g, as specified in greater detail elsewhere herein, is applied. In certain embodiments, the centrifugal force applied to the plant from about 1 second to about 180 minutes in duration, as specified in greater detail elsewhere herein. In certain embodiments, the plant is aligned with the direction of the centrifugal force during as described in detail elsewhere herein. In certain embodiments, the axis of the plant is maintained by a plant centrifugation support during the application of the centrifugal force. In certain embodiments, the plant centrifugation support maintains alignment of the axis of the plant with the direction of the centrifugal force within a certain degree. In certain embodiments, the plant is in direct contact with the plant centrifugation support and in certain embodiments, the plant is not in direct contact with the plant centrifugation support. In certain embodiments, the centrifugal force increases contact of the chromosome doubling agent with the shoot meristem over the contact of the shoot meristem with the chromosome doubling agent achieved by contacting it without centrifugation. In certain embodiments, the centrifugal force causes migration of the chromosome doubling agent such that the agent contacts a tissue of the plant not contacted when the plant was contacted to the chromosome doubling agent prior to the application of the centrifugal force. In certain embodiments, the corn plant is at the VE, V1, V2, V3, V4, V5, or V6 vegetative growth stage. In certain embodiments, the chromosome doubling agent is colchicine. In certain embodiments, the plant is contacted with the solution comprising the chromosome doubling agent for less than about 1 hour or 3 hours in duration, or for a duration described elsewhere herein, before the application of the centrifugal force.

Certain embodiments provide for methods for delivering a plant treatment agent to a plant tissue comprising contacting the surface of a plant with a solution that comprises the plant treatment agent and applying a centrifugal force to the plant contacted with the solution, wherein the axis of the plant is maintained by a plant centrifugation support (PCS) during the application of the centrifugal force, thereby delivering the plant treatment agent to the plant tissue. Unless otherwise stated, all of the parameters disclosed elsewhere herein for contacting a plant with a solution comprising a plant treatment agent and applying a centrifugal force are applicable to such methods. In certain embodiments, the PCS maintains alignment of the axis of the plant with the direction of the centrifugal force during step. In certain embodiments, the plant is in direct contact with the plant centrifugation support and in certain embodiments, the plant is not in direct contact with the plant centrifugation support. In certain embodiments, a centrifugal force of from about 10 g to about 500 g is applied. In certain embodiments, a centrifugal force of from about 500 g to about 4000 g is applied. In certain embodiments, the centrifugal force causes migration of the plant treatment agent such that the plant treatment agent contacts a tissue of the plant not contacted with the plant treatment agent when the plant is contacted with the plant treatment agent prior to centrifugation. In certain embodiments, application of the centrifugal force increase the contact of a selected plant tissue with the plant treatment agent over its contact with the plant treatment agent before application of the force. In certain embodiments, the plant tissue is a shoot meristem. In certain embodiments, the plant is a corn plant, for example a corn plant at the VE, V1, V2, V3, V4, V5, or V6 vegetative growth stage. In certain embodiments, the plant is a $DH_0$ plant. In certain embodiments, the plant treatment agent is a chromosome doubling agent, for example, colchicine. In certain embodiments, the centrifugal force increases contact of the chromosome doubling agent with the shoot meristem over the contact of the shoot meristem with the chromosome doubling agent achieved before application of the centrifugal force.

Certain embodiments provide methods for delivering a plant treatment agent to a plant tissue where a method comprises contacting the surface of a plant with a solution comprising the plant treatment agent and applying a first centrifugal force to the plant. Following the application of the first centrifugal force, the centrifugal force is removed. Then, a subsequent centrifugal force is applied to the plant subjected to the first centrifugal force. All of the parameters disclosed elsewhere herein for contacting a plant with a solution comprising a plant treatment agent and applying a centrifugal force are applicable to contacting the plant and both the first and subsequence applications of centrifugal force.

Unsubmerged Centrifugation

During an unsubmerged centrifugation, the target tissue is separated from the reserve treatment solution substantially throughout the application of centrifugal force. That is, in certain embodiments, there may be a period, generally relatively brief, wherein the selected tissue is submerged, for example, at the beginning and/or end of a centrifugation when a swinging-bucket centrifuge is building speed or slowing down and the reserve solution has not yet reached the location outside the plant where it will rest during centrifugation and/or re-accumulates on the plant.

Once a plant has been contacted with a solution comprising a plant treatment agent, such as by soaking in a body of liquid, the plant can be separated from the main body of solution used to contact the plant. Although the main body of solution used to contact the plant is separated from the plant, some solution will typically remain in contact with the surface of the plant, typically as droplets clinging to the surface, e.g., "coating" the plant surface, or otherwise retained for a period of time after the main body of the solution is removed.

When the selected tissue, or the plant surface surrounding the selected tissue, is/are contacted with treatment solution and properly aligned during centrifugation, some of the treatment agent remaining on or in the plant will be forced into the selected tissue of the plant by the force of acceleration generated during the unsubmerged centrifugation. This alignment will depend on the selected tissue and requires only the application of basic physical principles to determine an effective orientation. Treatment agent that leaves the plant during an unsubmerged centrifugation will move through the centrifuge container to join the reserve treatment agent at one end of the centrifuge container in the predictable way that liquids do.

In certain embodiments of this invention, less than 99%, or less than 98%, or less than 97%, or less than 96%, or less than 95%, or less than 94%, or less than 93%, or less than 92%, or less than 91%, or less than 90%, or less than 89%, or less than 88%, or less than 87%, or less than 86%, or less than 85%, or less than 84%, or less than 83%, or less than 82%, or less than 81%, or less than 80% of the plant surface remains in contact with the plant treatment agent during a centrifugation or at the end of a centrifugation.

In certain embodiments, the solution comprising the plant treatment agent is removed or substantially removed from the surface of the plant prior to and/or during the application of the centrifugal force, such that less than about 5%, less than about 4%, less than about 3%, less than about 2%, or less than about 1% of the surface of the plant surface remains in contact with the solution comprising the plant treatment agent by the end of the application of the centrifugal force without requiring additional removal of the solution.

For example, during unsubmerged centrifugations as described in the examples herein, all plant treatment agents that migrated from the surface of the plant during the centrifugation accumulated against the wall of the centrifuge container near the roots of the plant when the centrifugation was over. Because some of the roots were also in contact with this wall of the centrifugation container, the reserve liquid spread to a portion of the roots, and so they remained in contact with the treatment solution at the end of the centrifugation. Care was taken to limit this contact during an unsubmerged spin, including limiting the treatment solution used during the contacting step so that only a few mililiters of treatment solution collected in the centrifuge container during and/or after application of centrifugal force in a typical unsubmerged spin.

Certain embodiments provide for further separating the reserve treatment agent from the selected tissue using a variety of methods, including the incorporation of materials that absorb the reserve treatment agent. It is also provided that one could use a centrifuge container shaped such that it reserves the treatment solution during centrifugation in a place where the reserve treatment agent does not re-contact the selected tissue after migrating away from the plants during the application of centrifugal forces, or use an insertable partition to accomplish similar results. It is also provided that the reserve treatment agent exits the centrifuge container during centrifugation, e.g. with an opening at one end of the centrifuge container for liquid to exit during centrifugation. In that case, the reserve treatment agent does not rest inside the centrifuge container during application of a centrifugal force, but exits to a location where it does not contact the selected tissue during the application of a centrifugal force.

In certain embodiments, an axis of the plant is aligned relative with the centrifugal force. A plant can be described as having multiple axes. One of these is the shoot-root axis which runs in the direction of from the root-end up through the shoot-end and vice versa. In certain embodiments, the shoot-root axis of the plant is aligned with the direction of the centrifugal force. In certain embodiments, the shoot-root axis of the plant is substantially aligned with, for example within 3° of, the direction of the centrifugal force. In certain embodiments, the shoot-root axis of the plant is aligned within 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, or 30° of the direction of the centrifugal force.

In certain embodiments, the shoot-root axis of the plants is aligned with the direction of the centrifugal force during centrifugation and the plants are provided with a PCS to keep the plants from bending, buckling, collapsing, etc., during the application of the centrifugal force. In certain embodiments, the support prevents the plants from being damaged by the forces generated during centrifugation. In certain embodiments, the support allows a plant to recover from the application of a centrifugal force wherein the same plant without the support would be damaged beyond recovery. In certain embodiments, the support maintains or at least generally maintains the shoot-root axis of the plant by preventing it from bending, buckling, collapsing, etc.

In certain embodiments, the support maintains the alignment of an axis of a plant, such as the alignment of the shoot-root axis, relative to the direction of the centrifugal force. In certain embodiments, the support maintains the alignment of an axis of a plant, such as the alignment of the shoot-root axis, with the direction of the centrifugal force or at least substantially aligned with the direction of the centrifugal force, for example within 3° of, the direction of the centrifugal force. In certain embodiments, the support maintains the alignment of an axis of a plant, such as the alignment of the shoot-root axis, within 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, or 30° of the direction of the centrifugal force.

In certain embodiments, the support provides for the use of higher than anticipated centrifugation speeds/forces while keeping the plant from bending, buckling, collapsing, etc. In certain embodiments, the support provides for the use of higher than anticipated centrifugation speeds/forces while keeping the plant from being damaged by the forces generated during centrifugation. In certain embodiments, the support provides for the use of higher than anticipated centrifugation speeds/forces while allowing a plant to recover from the application of a centrifugal force, wherein the same plant without the support would be damaged beyond recovery.

In certain embodiments, use of a support structure as described herein allows for a centrifugal force of up to about 500 g, 750 g, 1000 g, 1250 g, 1500 g, 1750 g, 2000 g, 2250 g, 2500 g, 2750 g, 3000 g, 3500 g, or 4000 g to be applied to the plant. In certain embodiments, use of a support structure as described herein allows for a centrifugal force of from about 10 g or 20 g or 100 g or 300 g up to about 500 g, 750 g, 1000 g, 1250 g, 1500 g, 1750 g, 2000 g, 2250 g, 2500 g, 2750 g, 3000 g, 3500 g, or 4000 g to be applied to the plant. In certain embodiments, use of a support structure as described herein allows for a centrifugal force of at least about 500 g, 750 g, 1000 g, 1250 g, 1500 g, 1750 g, 2000 g, 2250 g, 2500 g, 2750 g, 3000 g, or 4000 g to be applied to the plant. In certain embodiments, the centrifugal force applied is from about 10 g to about 4000 g. In certain embodiments, the centrifugal force applied is from about 300 g to about 2000 g. In certain embodiments, the centrifugal force applied is from about 500 g to about 2000 g. In certain embodiments, the centrifugal force applied is from about 750 g to about 1250 g. In certain embodiments, the centrifugal force applied is from about 1000 g to about 1500 g. In certain embodiments, the centrifugal force applied is from about 1250 g to about 1750 g. In certain embodiments, the centrifugal force applied is from about 1500 g to about 2000 g. In certain embodiments, the centrifugal force applied is from about 1750 g to about 2250 g. In certain embodiments, the centrifugal force applied is from about 2000 g to about 2500 g. In certain embodiments, the centrifugal force applied is from about 2250 g to about 2750 g. In certain embodiments, the centrifugal force applied is from about 2500 g to about 3000 g. In certain embodiments, the centrifugal force applied is from about 2750 g to about 3250 g. In certain embodiments, the centrifugal force applied is from about 3000 g to about 3500 g. In certain embodiments, the centrifugal force applied is from about 3250 g to about 3750 g. In certain embodiments, the centrifugal force applied is from about 3500 g to about 4000 g. In certain embodiments, the centrifugal force applied is from any of about 500 g, 750 g, 1000 g, 1250 g, 1500 g, 1750 g, 2000 g, 2250 g, 2500 g, 2750 g, 3000 g, or 3500 g to any of about 750 g, 1000 g, 1250 g, 1500 g, 1750 g, 2000 g, 2250 g, 2500 g, 2750 g, 3000 g, 3500 g, or 4000 g.

In certain embodiments, the centrifugal force is applied to a plant and support structure for at least 1 second, 5 seconds, 10 seconds, 20 seconds, 30 seconds, 45 seconds, 1 minute, 2 minute, 3 minute, 4 minute 5 minute, 10 minutes, 20 minutes, 30 minutes, 45 minutes, 60 minutes, 120 minutes, or 180 minutes. In certain embodiments, the centrifugal force is applied to a plant and support structure for not more than about 5 seconds, 10 seconds, 20 seconds, 30 seconds, 45 seconds, 1 minute, 2 minute, 3 minute, 4 minute 5 minute, 10 minutes, 20 minutes, 30 minutes, 45 minutes, 60 minutes, 120 minutes, or 180 minutes. In certain embodiments, the centrifugal force is applied to a plant and support structure for between any of about 1 second, 5 seconds, 10 seconds, 20 seconds, 30 seconds, 45 seconds, 1 minute, 2 minute, 3 minute, 4 minute 5 minute, 10 minutes, 20 minutes, 30 minutes, 45 minutes, 60 minutes, or 120 minutes to any of about 5 seconds, 10 seconds, 20 seconds, 30 seconds, 45 seconds, 1 minute, 2 minute, 3 minute, 4 minute 5 minute, 10 minutes, 20 minutes, 30 minutes, 45 minutes, 60 minutes, 120 minutes, or 180 minutes.

Following an unsubmerged centrifugation, plants can be subjected to subsequent treatments (i.e. a serial centrifugation) or rinsed if desired, such as with water, to remove any remaining plant treatment solution, and then recovered by being transplanted in growth media and tended in a protected environment (e.g. greenhouse, shade house, growth room or growth chamber, tissue culture room, etc.) or transplanted directly to a field.

Submerged Centrifugation

During a submerged spin, the target tissue is submerged and/or remains in contact with the reserve treatment agent, i.e. the body of treatment agent in the centrifuge container that does not migrate into the plant. In certain embodiments, the rest of the plant body is also submerged and/or remains in contact with the reserve treatment agent in the centrifuge container during application of a centrifugal force. In certain embodiments, a PCS is used to support the target tissue of a plant, and/or the rest of the plant body, such that target tissue is submerged in treatment agent during the application of a centrifugal force while substantially the rest of the plant body is not submerged.

In certain embodiments following the initial contacting of the surface of the plant with the solution comprising the plant treatment agent, additional solution may be added to ensure that substantially most of the plant, and/or the targeted tissue, remains submerged and or in contact with the reserve treatment solution during application of the centrifugal force.

Despite the general reference to submerged herein, the method is not limited to requiring that the entire plant be submerged during centrifugation. In the submerged centrifugations conducted herein, we found that as long as the targeted tissue was submerged, and/or that the tissues on the surface of the plant surrounding the targeted tissue were submerged, good delivery of agent to the tissue could be obtained. In certain embodiments, wherein at least the selected tissue was submerged, and/or that the tissues on the surface of the plant surrounding the targeted tissue were submerged, good delivery of agent to the tissue were obtained.

In certain embodiments, a plant or plants are placed in a container and the solution comprising the plant treatment agent is poured over them until sufficiently submerged. In certain embodiments, only the selected tissue and/or surface tissues surrounding the targeted tissue remain in contact with the treatment agent during centrifugation.

For example, wherein the selected tissue is shoot apical meristem, less than about 1% of a plant's total surface area is contacted during a submerged centrifugation to achieve delivery of an agent to tissues of the SAM. In certain embodiments, less than about 1% of the surface of a plant needs to be in contact with the plant treatment agent during a submerged centrifugation in order to deliver the plant treatment agent to the targeted tissue.

In certain embodiments, at least about 1% or more of the plant surface need remain in contact with the plant treatment solution during a submerged centrifugation. In certain embodiments, at least about 1%, 2%, 3%, 4%, 5%, 6%, 7%, 8%, 9%, 10%, 15%, 20%, 25%, 30%, 40%, 50%, 60%, 70%, 80%, 90%, 95%, 99%, or 100% of the surface of the plant of the plant surface is submerged in the plant treatment agent during centrifugation.

In certain embodiments, a plurality of plants is placed in a container also holding a reservoir of solution comprising a plant treatment agent such that the plurality of plants are bundled together in the solution. Although the plants will be generally submerged, some of the plants may not have all of their surfaces covered at all times. In certain embodiments, the plants are mixed or agitated in the treatment agent at least once before centrifugation to help ensure that all of the plant surfaces are contacted by the treatment agent at some point before or during centrifugation.

In certain embodiments, the plants and/or the axes of the plants, need not be arrayed or aligned relative to one another and/or relative to the force of acceleration during centrifugation. For example, in certain embodiments, a plurality such as about a dozen, about several dozen, about 50, about 75, about 100, etc. seedlings can be placed into the reservoir of liquid comprising the plant treatment solution and allowed to mix about before and/or during centrifugation. In certain embodiments, no attention is paid to the alignment of the plants. In certain other embodiments, two or more of the plurality of plants or their axes are intentionally aligned relative to each other. In certain embodiments, at least about 5%, 10%, 20%, 25%, 30%, 40%, 50%, 60%, 70%, 75%, 80%, 90%, 95%, 98%, 99%, or 100% of the plurality of plants or their axes are aligned relative to each other during centrifugation, whether intentional or not. For example aligning and/or bundling plants together during so that they will be ready for additional downstream steps, such as additional one or more additional centrifugation steps, following the first centrifugation. Alignment and/or bundling prior to the first centrifugation can make performing subsequent steps, such as centrifugation in certain embodiments wherein the alignment of the plants is also performed, more efficient.

In certain embodiments, the amount of surface area of the plant that is contacted with a plant treatment agent can vary with the type of plant and/or the structure of the plant, the size of the plant, the tissue to which the plant treatment agent is to be delivered, the developmental stage of the plant, and the amount of solution comprising the plant treatment agent available for use, among other factors. In certain embodiments, between about 1% and 100% of the plant surface is contacted with the plant treatment agent. In certain embodiments, between about 5% and 100% of the plant surface is contacted with the plant treatment agent. In certain embodiments, at least about 1%, or at least about 2%, or at least about 5%, or at least about 10%, or at least about 20%, or at least about 30%, or at least about 40%, or at least about 50%, or at least about 60%, or at least about 70%, or at least about 80%, or at least about 90%, or at least about 95%, or at least about 98%, or at least about 99%, or about 100% (for example the plant is completely submerged in the solution) of the surface of the plant remains contacted with the solution comprising the plant treatment agent during centrifugation.

In certain embodiments wherein at least a portion of the plant surface remains contacted or submerged during centrifugation, a centrifugal force of up to about 20 g, 40 g, 50 g, 60 g, 70 g, 75 g, 80 g, 90 g, 100 g, 150 g, 200 g, 250 g, 300 g, 350 g, 400 g, 450 g, 500 g, 550 g, 600 g, 650 g, 700 g, 750 g, 800 g, 850 g, 900 g, 950 g, 1000 g, 1050 g, 1100 g, 1150 g, 1200 g, 1250 g, 1300 g, 1350 g, 1400 g, 1450 g, 1500 g, 1550 g, 1600 g, 1650 g, 1700 g, 1750 g, 1800 g, 1850 g, 1900 g, 1950 g, 2000 g, 2050 g, 2100 g, 2150 g, 2200 g, 2250 g, 2300 g, 2350 g, 2400 g, 2450 g, 2500 g, 2550 g, 2600 g, 2650 g, 2700 g, 2750 g, 2800 g, 2850 g, 2900 g, 2950 g, 3000 g, 3050 g, 3100 g, 3150 g, 3200 g, 3250 g, 3300 g, 3350 g, 3400 g, 3450 g, 3500 g, 3550 g, 3600 g, 3650 g, 3700 g, 3750 g, 3800 g, 3850 g, 3900 g, 3950 g, or 4000 g may be applied. In certain embodiments wherein at least a portion of the plant surface remains contacted or submerged during centrifugation, a centrifugal force of at least about 10 g, 20 g, 40 g, 50 g, 60 g, 70 g, 75 g, 80 g, 90 g, 100 g, 150 g, 200 g, 250 g, 300 g, 350 g, 400 g, 450 g, 500 g, 550 g, 600 g, 650 g, 700 g, 750 g, 800 g, 850 g, 900 g, 950 g, 1000 g, 1050 g, 1100 g, 1150 g, 1200 g, 1250 g, 1300 g, 1350 g, 1400 g, 1450 g, 1500 g, 1550 g, 1600 g, 1650 g, 1700 g, 1750 g, 1800 g, 1850 g, 1900 g, 1950 g, 2000 g, 2050 g, 2100 g, 2150 g, 2200 g, 2250 g, 2300 g, 2350 g, 2400 g, 2450 g, 2500 g, 2550 g, 2600 g, 2650 g, 2700 g, 2750 g, 2800 g, 2850 g, 2900 g, 2950 g, 3000 g, 3050 g, 3100 g, 3150 g, 3200 g, 3250 g, 3300 g, 3350 g, 3400 g, 3450 g, 3500 g, 3550 g, 3600 g, 3650 g, 3700 g, 3750 g, 3800 g, 3850 g, 3900 g, 3950 g, or 4000 g may be applied. In certain embodiments, the centrifugal force applied is from any of about 10 g, 20 g, 40 g, 50 g, 60 g, 70 g, 75 g, 80 g, 90 g, 100 g, 150 g, 200 g, 250 g, 300 g, 350 g, 400 g, 450 g, 500 g, 550 g, 600 g, 650 g, 700 g, 750 g, 800 g, 850 g, 900 g, 950 g, 1000 g, 1050 g, 1100 g, 1150 g, 1200 g, 1250 g, 1300 g, 1350 g, 1400 g, 1450 g, 1500 g, 1550 g, 1600 g, 1650 g, 1700 g, 1750 g, 1800 g, 1850 g, 1900 g, 1950 g, 2000 g, 2050 g, 2100 g, 2150 g, 2200 g, 2250 g, 2300 g, 2350 g, 2400 g, 2450 g, 2500 g, 2550 g, 2600 g, 2650 g, 2700 g, 2750 g, 2800 g, 2850 g, 2900 g, 2950 g, 3000 g, 3050 g, 3100 g, 3150 g, 3200 g, 3250 g, 3300 g, 3350 g, 3400 g, 3450 g, 3500 g, 3550 g, 3600 g, 3650 g, 3700 g, 3750 g, 3800 g, 3850 g, 3900 g, 3950 g, or 4000 g.

In certain of such embodiments, the centrifugal force is applied for at least 1 second, 5 seconds, 10 seconds, 20 seconds, 30 seconds, 45 seconds, 1 minute, 2 minute, 3 minute, 4 minute 5 minute, 10 minutes, 20 minutes, 30 minutes, 45 minutes, 60 minutes, 120 minutes, or 180 minutes. In certain embodiments, the centrifugal force is applied to a plant and support structure for not more than about 5 seconds, 10 seconds, 20 seconds, 30 seconds, 45 seconds, 1 minute, 2 minute, 3 minute, 4 minute 5 minute, 10 minutes, 20 minutes, 30 minutes, 45 minutes, 60 minutes, 120 minutes, or 180 minutes. In certain embodiments, the centrifugal force is applied to a plant and support structure for between any of about 1 second, 5 seconds, 10 seconds, 20 seconds, 30 seconds, 45 seconds, 1 minute, 2 minute, 3 minute, 4 minute 5 minute, 10 minutes, 20 minutes, 30 minutes, 45 minutes, 60 minutes, or 120 minutes to any of about 5 seconds, 10 seconds, 20 seconds, 30 seconds, 45 seconds, 1 minute, 2 minute, 3 minute, 4 minute 5 minute, 10 minutes, 20 minutes, 30 minutes, 45 minutes, 60 minutes, 120 minutes, or 180 minutes.

In certain embodiments, the duration of time from when the plant surface is contacted with the solution comprising the plant treatment agent, and when it is removed, is for at least about one second, 5 seconds, 30 seconds, one minute, five minutes, ten minutes, 20 minutes, 30 minutes, 45 minutes, 1 hour, 1.5 hours, 2 hours, 2.5 hours, 3 hours or longer. In certain embodiments, the duration of time from when the plant surface is contacted with the solution comprising the plant treatment agent and when it is removed is no greater than about 5 seconds, 30 seconds, one minute, five minutes, ten minutes, 20 minutes, 30 minutes, 45 minutes, 1 hour, 1.5 hours, 2 hours, 2.5 hours, 3 hours or longer. In certain embodiments, the duration of time from when the plant surface is contacted with the solution comprising the plant treatment agent and when it is removed is from any of about one second, 5 seconds, 30 seconds, one minute, five minutes, ten minutes, 20 minutes, 30 minutes, 45 minutes, 1 hour, 1.5 hours, 2 hours, or 2.5 hours to about 5 seconds, 30 seconds, one minute, five minutes, ten minutes, 20 minutes, 30 minutes, 45 minutes, 1 hour, 1.5 hours, 2 hours, 2.5 hours, or 3 hours.

The amount of the surface of the plant that is contacted with the plant treatment agent can vary by, for example, the method through which the surface of the plant is contacted with the plant treatment agent and/or by, for example, the amount, such as volume, of the plant treatment agent that is used. For example, a plant treatment agent may be sprayed or misted generally over the entire surface of a plant or over only certain portions.

If a liquid treatment solution is used, the greater the volume of plant treatment agent added to the container, the easier it is to ensure that plants treated in the container are sufficiently contacted, up until the plants are substantially completely submerged and/or they begin to float to the surface of the liquid. Further, as additional plants are added to the centrifuge container, the volume in the container available to treatment agent will diminish, thus decreasing the volume of treatment agent needed to contact the required surface on each plant. Also, if the container containing the plant(s) and the plant treatment agent is agitated, such as by shaking or tumbling, to distribute the plant treatment agent throughout the container, generally the greater the surface area of the plant that will be contacted with the plant treatment agent.

In certain embodiments, the plant is a corn seedling with leaves that form a cup or whorl as they unfold. This area at the base of the unfurling leaves is capable of holding liquid. In certain embodiments, the solution comprising the plant treatment agent is contacted with the corn plant without regard to whether liquid is placed into the cup or whorl. In certain embodiments, wherein the solution comprising the plant treatment agent is contained within the cup or whorl, an additional surface area of the corn plant is also contacted with the solution comprising the plant treatment agent. In certain embodiments, the additional surface area of the corn plant that is also contacted with the solution comprising the plant treatment agent is greater than about 1%, 2%, 3%, 4%, or 5% more than the surface area contacted within cup/whorl. In certain embodiments, at least a portion of the surface of the plant is contacted with the solution comprising the plant treatment agent but no solution is placed into the cup/whorl formed at the base of the unfurling leaves, that is, the cup/whorl is devoid of solution prior to the application of a centrifugal force.

Centrifugation Treatments

Certain embodiments of the invention employ "serial centrifugations" which include more than one centrifugation conducted in serial and may include at least one unsubmerged centrifugation and/or one submerged centrifugation. During a serial centrifugation, plants are subjected to at least one additional centrifugation following the application of a first centrifugation. A serial centrifugation may include multiple centrifugations of any type, in any order, with various steps before, after, or between centrifugations. A serial centrifugation may incorporate the use of a PCS during the application of an accelerative force generated during at least one centrifugation treatment. A "double centrifugation" is a type of serial centrifugation comprising two centrifugations conducted in serial or at different times.

In certain embodiments, a serial centrifugation comprises a first submerged spin followed by an unsubmerged spin.

In certain embodiments, a centrifugal force is applied to a plant wherein the targeted tissue is submerged in reserve treatment agent during the application of a centrifugal force. In certain embodiments, at least 1% of the total plant surface is contacted with a solution comprising a plant treatment agent during application of the centrifugal force. In certain embodiments, at least about 1%, or at least about 2%, or at least about 3%, or at least about 5%, or at least about 10%, or at least about 20%, or at least about 30%, or at least about 40%, or at least about 50%, or at least about 60%, or at least about 70%, or at least about 80%, or at least about 90%, or at least about 95%, or at least about 98%, or at least about 99%, or 100% of the plant surface is contacted with the solution comprising the plant treatment solution during application of the centrifugal force.

In certain embodiments the solution comprising the plant treatment agent is removed or substantially removed from the surface of the plant before and/or during the application of the subsequent centrifugal force such that less than about 5%, less than about 4%, less than about 3%, less than about 2%, or less than about 1% of the surface of the plant remains in contact with the solution by the end of the application of the subsequent centrifugal force.

The centrifugal forces applied to a plant during a centrifugation that is part of a serial centrifugation can be any centrifugal force known in the art. In certain embodiments, the centrifugation parameters of at least one centrifugation treatment are consistent with those described elsewhere herein, such as of a submerged centrifugation or an unsubmerged centrifugation or a serial centrifugation, as described elsewhere herein. These include the ranges of centrifugation forces between 10-4000 g during an unsubmerged spin and/or 10-500 g during a submerged spin and the duration of the centrifugal force applied to the plants could include a range from about one second to about 180 minutes.

Following a first centrifugation treatment, plants can be subjected to subsequent or serial treatments, or rinsed, such as with water, to remove any remaining plant treatment solution, and then recovered by being transplanted in growth media and tended in a protected environment (e.g. greenhouse, shade house, growth room or growth chamber, tissue culture room, etc.) or transplanted directly to a field.

Plant Centrifugation Supports

In certain embodiments, structural support inside the centrifuge container is included with the plants when they are centrifuged. In certain embodiments, a plant centrifugation support (PCS) maintains a desired orientation of the targeted tissue relative to the force of acceleration generated by the centrifugation such that at least some portion of the treatment agent contacting the plant migrates to and/or is forced into the selected tissue by the force of acceleration generated during centrifugation, i.e. to "properly align" the target tissue and/or plant. In certain embodiments, a PCS supports at least some portion of a plant during centrifugation such that the cells of the target tissue do not contact the reserve treatment agent. In certain embodiments, a PCS eliminates or mitigates cell, tissue, or organ damage to the plant caused during the application of a centrifugal force, although this is not necessarily always required as a user might find utility in recovering damaged plants containing cells or tissue wherein treatment agent was successfully delivered during centrifugation.

Figure 5:
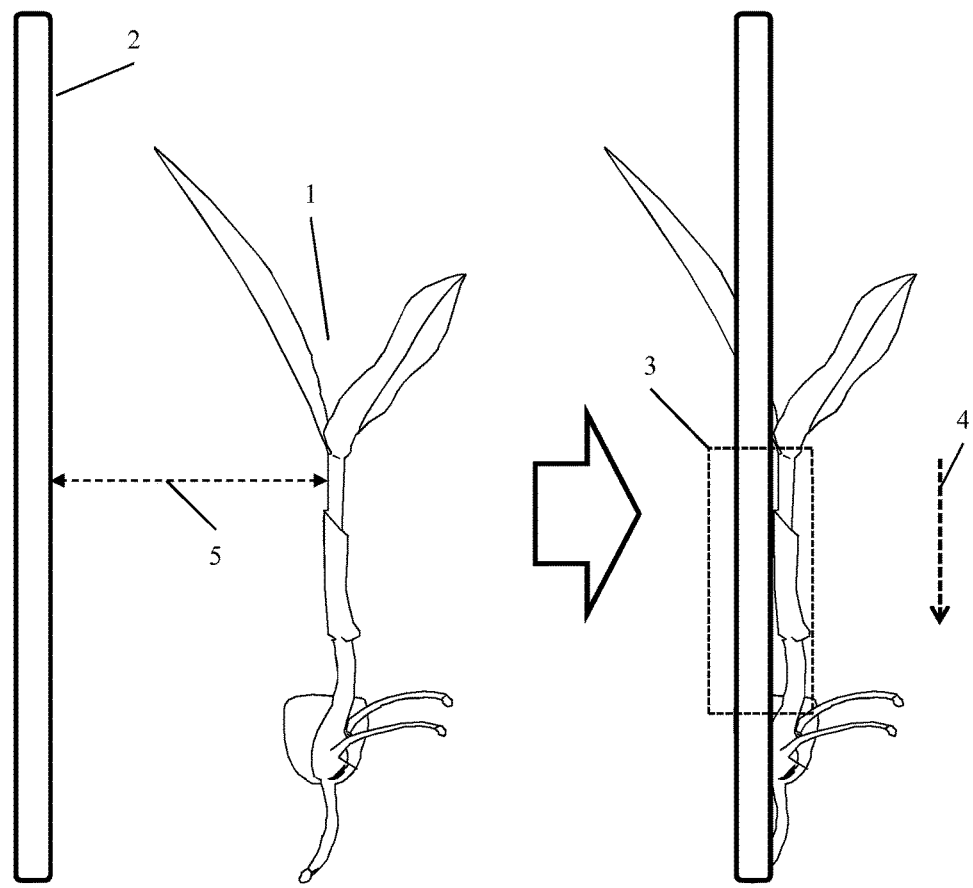
FIG. 5 shows an example of a plant seedling 1 individually associated with (e.g., wrapped to) a single plant centrifuge support (PCS) 2 and reveals how seedlings 1 can be arranged relative to a PCS 2 and relative to the force of acceleration generated during centrifugation 4, such as when delivering plant treatment agents to the meristems of corn seedlings. The dashed box 3 represents an area of the plant where seedlings can be secured to a PCS 2. Other orientations of the plant 1 relative to the force of acceleration 4 can be used when certain other tissues of the plant are targeted. The double-headed, dashed horizontal line 5 indicates that the seedling and PCS can be brought into contact with one another.
Figure 6:
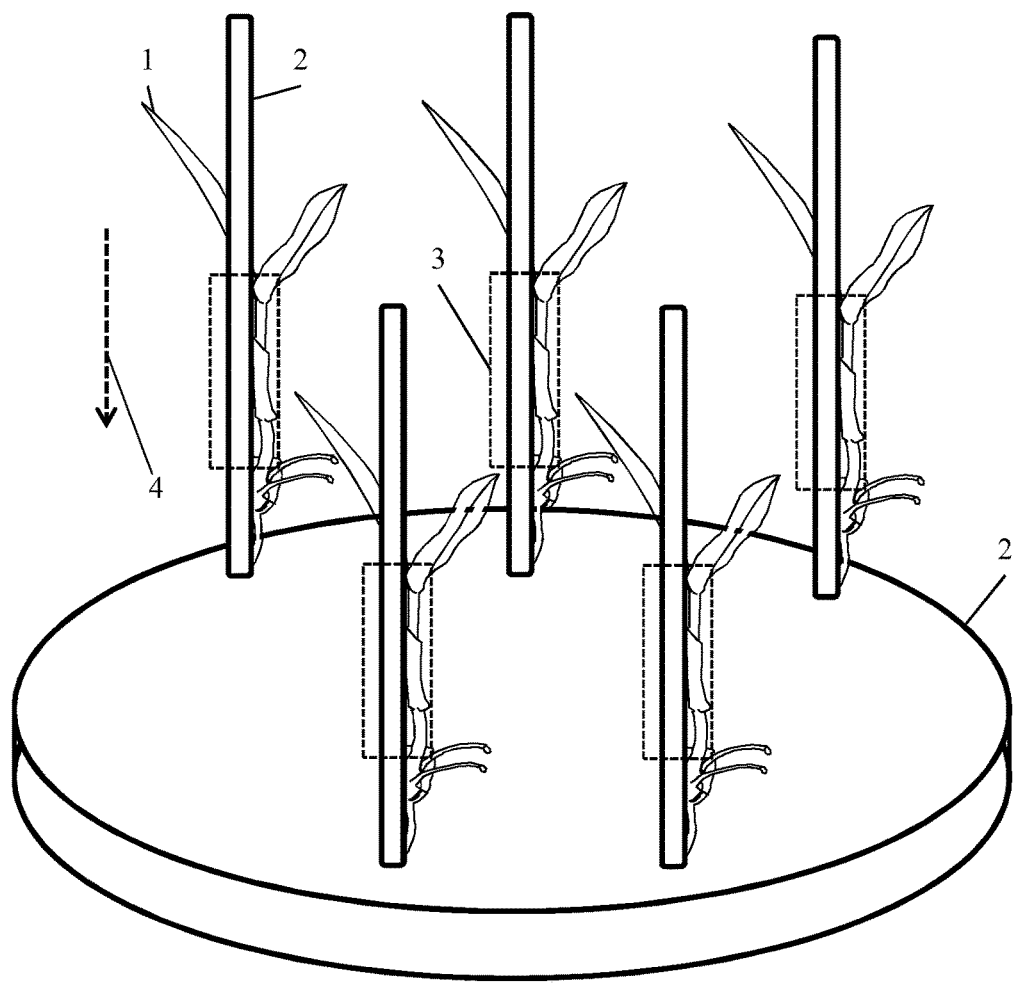
FIG. 6 shows an example of multiple seedlings 1 individually associated with a plant centrifuge support, e.g., in this illustrative example, wrapped and supported by a PCS 2 that comprises multiple rods. The dashed box 3 represents an area of the plant where seedlings can be secured to a PCS 2 in order to align the plants relative to the force of acceleration 4 generated during centrifugation, such as when the target tissue is the shoot apical meristem (SAM). Other orientations of the plant 1 relative to the force of acceleration 4 can be used when certain other tissues of the plant are targeted.
Figure 8:
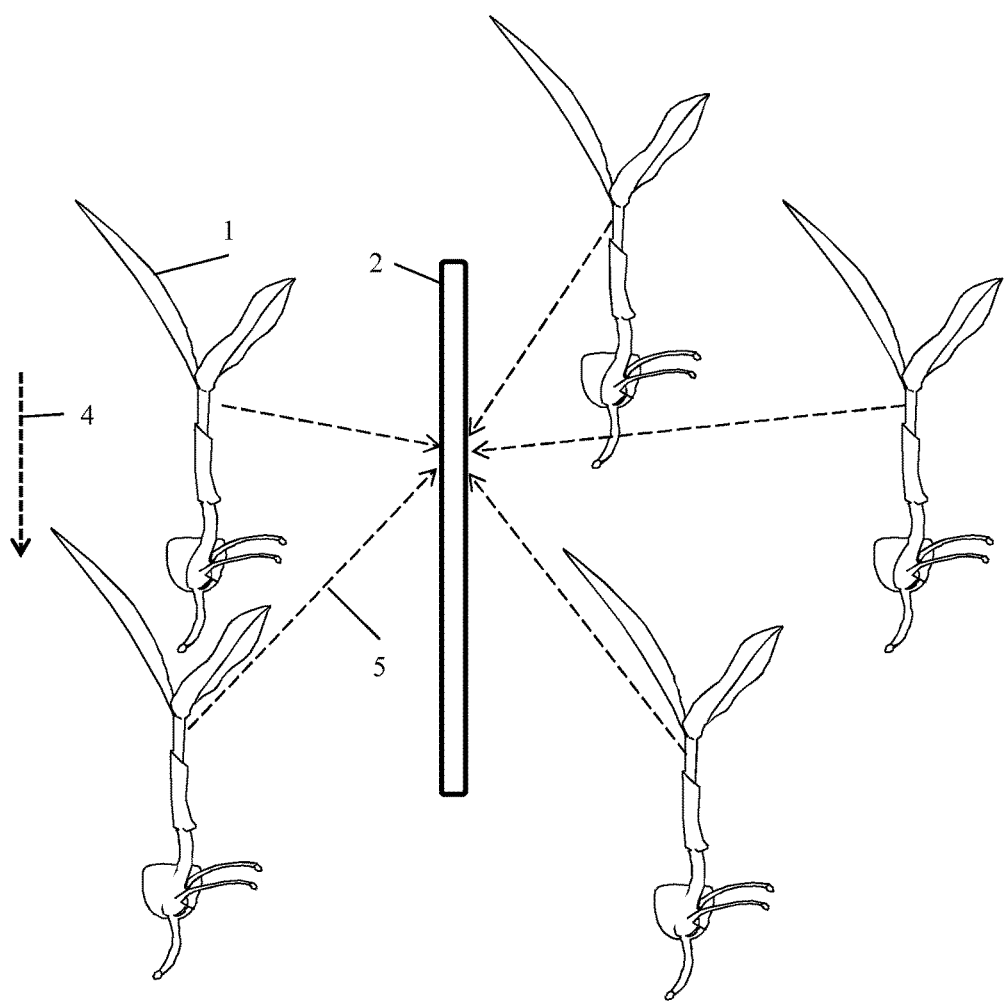
FIG. 8 shows one example of how multiple seedlings 1 can be associated with (in this illustrative example, attached to) a single PCS 2 relative to the force of acceleration generated during centrifugation 4 when delivering plant treatment agents to the meristems of corn seedlings 1. Other orientations of the plant 1 relative to the force of acceleration 4 can be used when certain other tissues of the plant 1 are targeted. The double-headed, dashed horizontal line 5 indicates that the seedlings and PCS can be brought into contact with one another.

In certain embodiments, a PCS is fixed to the inside of the centrifuge container, whether it be a removably connectable insert or whether it is molded or fitted into or otherwise attached permanently to the centrifuge container. In certain embodiments the PCS comprises at least one rod, pole, ridge, or fin that is attachable to a plant stem. In some embodiments the PCS comprises at least one approximately ⅛" diameter rod that is attachable to at least one plant, such as a plant seedling. In some embodiments, more than one plant is associated with, such as attached to, a PCS. FIG. 5 shows one example of a PCS. In some embodiments, more than one plant is attached to a PCS, whether each plant is individually-secured to different parts of a common PCS, as shown in FIG. 8, or whether more than one plant is attached to the same part of a common PCS, as shown in FIG. 6.

In certain embodiments, a PCS comprises an approximately ⅛" diameter wooden rod. In certain embodiments, the PCS is approximately the length of a plant to be centrifuged. In certain embodiments, this length of the PCS includes the length of the plant plus a length or width of a seed still attached to a seedling.

In certain embodiments, the PCS comprising a rod is set in the centrifuge sample container with one end, tip, or nose of the rod resting against the inside wall of the centrifuge sample container such that some portion of the rod extends into or across the interior of the centrifuge sample container. FIGS. 5-9 reveal various example embodiments of this.

In certain embodiments, substantial regions, such as at least about 5%, 10%, 20%, 25%, 30%, 40%, 50%, 60%, 70%, 75%, 80%, 90%, 95%, 98%, 99%, or 100%, of a plant stem are supported by a side of the PCS that the plant is associated with, for example attached to or secured by, and the PCS is set into the centrifuge sample container such that when the plant is centrifuged, the PCS holds the long axis of the plant stem parallel to the acceleration caused by the centrifugation. In certain embodiments, the long axis is the root-shoot axis of the plant. In certain embodiments, at least one plant is associated with, such as attached to, at least one PCS and the plant-PCS combination is centrifuged. In certain embodiments, the PCS contacts every plant it supports. In certain embodiments, the PCS provides sufficient support to the plants it contacts that the plants contacting it are able to provide sufficient support to other nearby plants that do not contact the PCS such that even plants not in direct contact with the PCS are sufficiently supported during centrifugation to satisfy the requirements of an unsubmerged centrifugation, described elsewhere herein.

As provided herein, a PCS can comprise any material sufficiently robust so as to prevent the target tissue from contacting the reserve treatment agent during centrifugation and/or to maintain a desired alignment of the target tissue during centrifugation. In certain embodiments, the PCS also prevents mortal damage to the plant that would otherwise be caused by collapsing, folding, tearing, shearing or breaking of the plant's organs and/or tissues during centrifugation. Similarly, a plant can be associated with a PCS in any manner, so long as the plant-PCS combination provides sufficient structural support to the plant so as to either prevent the target tissue from contacting the reserve treatment agent during centrifugation and/or to maintain a desired alignment of the target tissue during centrifugation. In certain embodiments, the PCS also prevents accelerative forces generated during centrifugation from damaging the plant's organs or tissues beyond recovery.

In certain embodiments, the PCS is at least as long as the stem of the plant to which it is associated with. In certain embodiments, the length of the PCS also depends on whether the seed remains attached to a seedling. In certain embodiments, the stem of a seedling is attached along the length of a PCS comprising a wooden rod approximately as long as the seedling or longer. In certain embodiments, a plant stem attached to a PCS with a wrap comprising flexible material such as a plastic paraffin, plastic wrap, aluminum foil, or any other material used to non-destructively and removably attach one item to another, including loops of string, wire, rubber bands, etc. Other forms of associating, attaching, or securing a plant to a PCS are envisioned, as long as the combination of PCS and plant provides sufficient friction to the surface of the plant so as to either prevent the target tissue from becoming submerged in reserve treatment agent during application of a centrifugal force and/or as long as the combination of PCS and plant maintains an alignment of the target tissue such that at least some treatment agent is pushed into contact with at least one cell of the target tissue during application of a centrifugal force.

In certain embodiments, the friction that holds the plant in place during centrifugation is created between the plant and the PCS directly, for example, when plants are individually wrapped to a single PCS. In certain embodiments, the association between the PCS and the plant can be indirect, such as wherein the friction that holds the plant in place occurs between at least two plants which are bundled together. In certain embodiments, this bundling is tight enough to provide the necessary friction to prevent the target tissue from becoming submerged in reserve treatment agent during application of a centrifugal force and/or maintain an alignment of the target tissue such that at least some target agent is pushed into contact with at least one cell of the target tissue during application of a centrifugal force.

In certain embodiments, a PCS can be a supporting foam that fills spaces around a plant such that it provides the friction necessary to prevent the target tissue from becoming submerged in reserve treatment agent during application of a centrifugal force and/or provides the friction necessary to maintain an alignment of the target tissue such that at least some target agent is pushed into contact with at least one cell of the target tissue during application of a centrifugal force. In a preferred embodiment, a PCS comprising a foam will also prevent the plants from suffering mortal damage during centrifugation. Any other type of supportive and/or adhesive matrix that satisfies the general description of a PCS mentioned previously herein could be used in conjunction with this invention.

Figure 9:
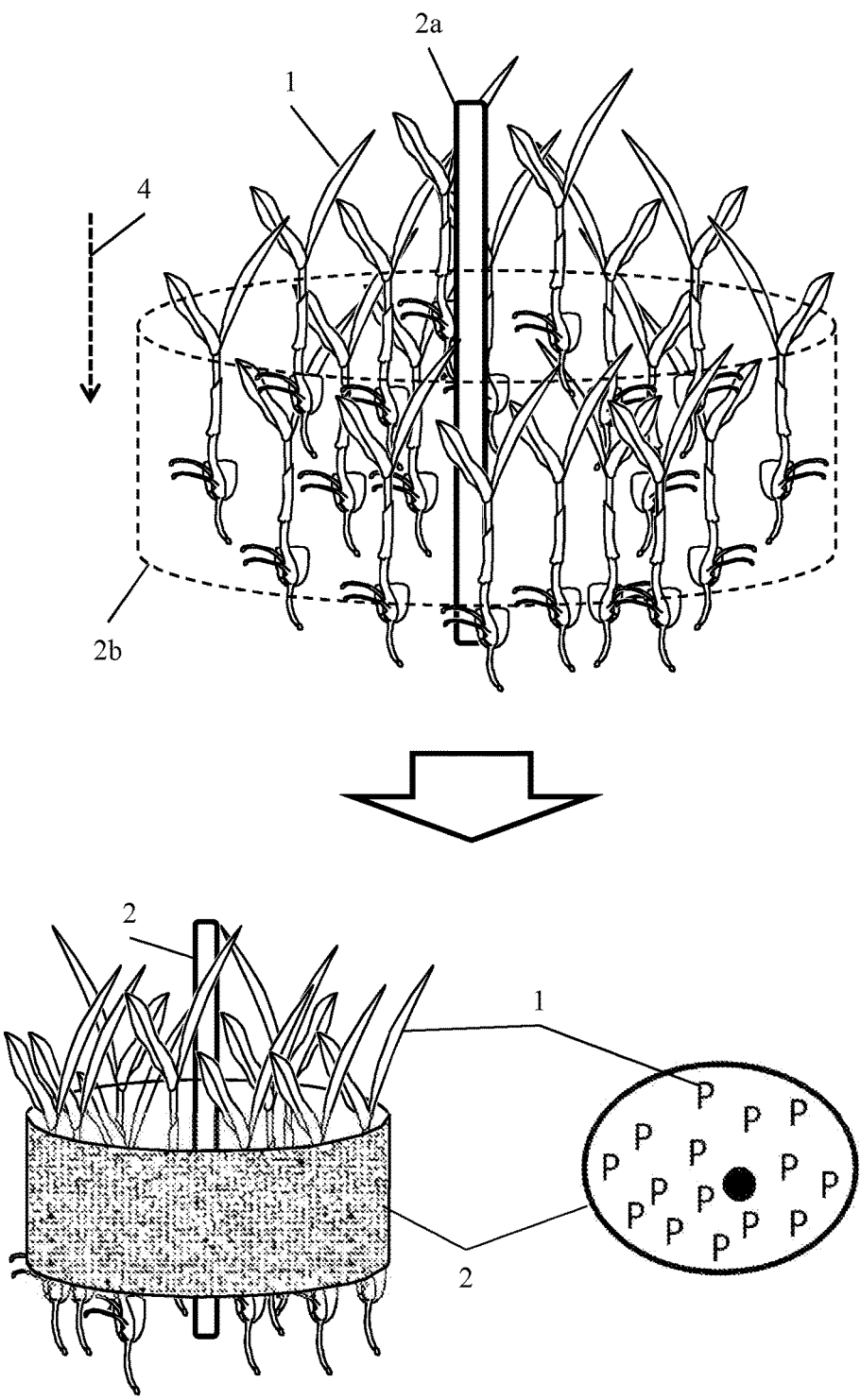
FIG. 9 shows one example of how plants 1 can be bundled into a PCS 2 that comprises a rod 2a and a wrap 2b. In the top portion of the figure, the wrap 2b is transparent and outlined by dashed lines and the space between seedlings 1 has been expanded for clarity. In the lower left portion of the figure, the wrap is shown surrounding the stems and other part parts of the plants in a way that reflects how a bundled PCS used in the experiments described herein appeared when it was placed into the centrifuge container prior to centrifugation. The lower right portion of the figure is a representation of the top-down view of the bundled PCS that is shown in the lower left. The letter P (for plant) in the top-down view is used to show one possible arrangement of the plant stems in relation to one another and the wrap and rod (filled black circle) of the bundle PCS. A bundle PCS like this could comprise more than one rod for support.

In certain embodiments, a PCS is associated with a collection of many plants bundled together and surrounded by a wrap, which in this embodiment is also a component of the PCS that helps provide the friction necessary for the PCS to fulfill its function (e.g., a wrap-rod PCS system). In certain embodiments, the rods are wrapped in with the plants in such a manner as to further improve performance of the wrap-rod PCS system. FIG. 9 illustrates and exemplary embodiment of a PCS system.

These methods are not limited to any specific alignment of a target tissue or of the plant during centrifugation. In certain embodiments, different tissues call for different orientations of the target tissue and or different orientations of the plant body relative to the force of acceleration generated during a centrifugation. For example, if the targeted tissue is a SAM, a PCS could be used to prevent the SAM from becoming submerged or from contacting the reserve treatment agent during application of a centrifugal force. The PCS could also be used to ensure that at least some of the treatment agent contacting the SAM, or the tissues surrounding the SAM, e.g. leaf primordia, and/or older leaves surrounding the SAM, at the beginning of a centrifugation is pushed into at least one cell of the SAM.

For example, described herein are methods wherein a treatment agent is delivered to corn SAMs. As illustrated by examples herein, plants were arranged in a Beckman Coulter Allegra X-14 series centrifuge such that the PCS would hold the shoot-root axis plants of the plants relatively parallel with the force of acceleration generated by centrifugation with the SAM ends of the plants nearest the center of the centrifuge and the root ends of the plants furthest from the center of the centrifuge. In this way, the force of acceleration generated during centrifugation will push some treatment agent near or at the surface of the SAM into at least one cell of the SAM during centrifugation.

In certain embodiments of an unsubmerged centrifugation targeting SAM tissue, several dozen haploid seedlings are bundled together in a PCS comprising a wrap and rod, and aligned substantially in the same orientation, similar to that shown in FIG. 9. The plants are then contacted by a doubling agent (e.g. colchicine) solution for several minutes, then placed in a centrifuge container and centrifuged such that the SAMs do not contact the reserve doubling agent and yet some of the doubling agent that was contacting the plant at the beginning of centrifugation is forced into at least one cell of the SAM during application of a centrifugal force, thereby delivering doubling agent to cells within the SAM of the plants. In a preferred embodiment, the bundle PCS also prevents mortal damage to the plants caused by accelerative forces generated during centrifugation. In some embodiments, a PCS can comprise a wrap or matt as long as it serves a function of a PCS described herein.

A PCS could be used in conjunction with substantially any centrifugation treatment, regardless of whether it performs the functions described above. For example, a user may elect to use a PCS during a submerged spin even though the PCS in that case does not prevent the target tissue from being submerged in reserve solution and even though alignment of the target tissue during a submerged centrifugation is not necessary. In certain embodiments, a PCS is used during a submerged centrifugation to align the plants and/or the targeted tissue and enable more efficient delivery of treatment solution to a targeted plant tissue. In certain embodiments, a PCS is used during a submerged centrifugation to keep the target tissue submerged in reserve treatment agent during centrifugation while keeping the rest, or substantially the rest, of the plant body out of the reserve treatment agent. In certain embodiments, a PCS is used during a submerged centrifugation because it makes processing plants before or after a centrifugation, or before or after a subsequent centrifugation, easier or more efficient.

Improving Doubling Efficiencies

Methods provided herein can be used to aid delivery of plant treatment agent comprising chromosome doubling agents to selected haploid plant tissues, thus improving doubling efficiencies.

"Doubling Efficiency" (DE) is an overall gauge of DH success calculated by dividing the number of $DH_0$ plants of a designation that produce $DH_1$ seed by the total number of $DH_0$ plants of that designation that were subjected to a chromosome doubling treatment.

As used herein, haploid plants, such as haploid seedlings, subjected to a chromosome doubling treatment are termed $DH_0$ plants. Successfully doubled $DH_0$ plants can produce haploid egg and/or sperm, and if the $DH_0$ plants are successfully selfed, the zygotic chromosome number can be recovered in substantially homozygotic offspring (termed $DH_1$ plants herein), with the vigor and fertility expected of a 2n sporophyte.

Certain embodiments provide methods of obtaining a doubled-haploid corn embryo comprising: performing any of the aforementioned methods of delivering a plant treatment agent to a plant tissue, wherein the plant is a haploid plant, and wherein the treatment agent is a chromosome doubling agent and wherein the doubling agent induces formation of at least one doubled-haploid plant. Also provided herein are methods of obtaining a doubled-haploid plant comprising: harvesting a doubled-haploid embryo from a seed obtained from by the methods described herein. In certain embodiments, the seed is attached to the ear of corn as the embryo is harvested from the seed. In other embodiments, the seed is not attached to the ear of corn as the embryo is harvested. Certain embodiments also provide supplying sufficient nutrients to a doubled-haploid embryo to permit development of the doubled-haploid embryo into a doubled-haploid plant.

Certain embodiments also provide methods of obtaining a doubled-haploid corn plant comprising: obtaining a doubled-haploid maize embryo derived by any of the methods provided herein and supplying sufficient nutrients to the embryo to permit development of the embryo into the doubled-haploid corn plant seed. A doubled-haploid corn embryo can be formed by methods comprising: performing any of the aforementioned methods of delivering a solution comprising a plant treatment agent into the shoot apical meristem, wherein the plant treatment agent is a chromosome doubling agent, and allowing the doubling agent to induce chromosome doubling.

Also provided are methods of obtaining a seed comprising a doubled-haploid corn embryo comprising: harvesting a seed comprising a doubled-haploid embryo obtained by the methods of obtaining a doubled-haploid corn embryo. A doubled-haploid corn embryo can be obtained by methods comprising: performing any of the aforementioned methods of delivering a plant treatment agent to a plant tissue, wherein the embryo treatment agent is a chromosome doubling agent, and allowing the doubling agent to induce formation of at least one doubled-haploid embryo in at least one of the seeds. In certain embodiments, the harvested seed is a physiologically mature seed.

Also provided are methods of obtaining a doubled-haploid corn plant comprising: sowing a seed comprising a doubled-haploid maize embryo obtained by the methods of obtaining a seed comprising a doubled-haploid corn embryo and permitting the sown seed to develop a doubled-haploid corn plant. In certain embodiments, the seed comprising the doubled-haploid corn embryo is obtained from a third party. In other words, the party who harvested the seed is not necessarily the party who sowed the seed comprising the doubled-haploid embryo and permitted the sown seed to develop into the doubled-haploid corn plant.

Additional Definitions and Descriptions

A "population of plants" or "plant population" means a set comprising any number, including one, of individuals, objects, or data from which samples are taken for evaluation, e.g. estimating QTL effects. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-10% of a population is what is commonly selected to be used in subsequent crosses in order to improve the performance of subsequent generations of the population.

As used herein, "cultivate" describes any activity that promotes or improves the growth of a plant at any point in its life cycle, including germination. "Tend" is used herein synonymously with cultivate, e.g. tending plants in a greenhouse is equivalent to cultivating plants in a greenhouse.

A "growth media" as used herein comprises any substrate capable of supporting the development of a plant including potting soil, field soil, and laboratory media, including but not limited to N6 or MS-based plant tissue culture media.

As used herein, "germination" describes a point in a plant life cycle that begins when the root radical first emerges from the seed coat. This time period can overlap the timeframe recognized as "sprouting", during which the seed begins to put out shoots.

The following disclosed embodiments are merely representative of the invention which may be embodied in additional forms. Thus, specific structural, functional, and procedural details disclosed herein are not to be interpreted as limiting.

EXAMPLES

Haploid corn plants used herein were obtained by pollinating F1 or F2 corn plants with pollen from a haploid inducer line. Ears were harvested when the seeds were mature, shelled, and the haploid seeds recovered by standard methods of the art.

Non-limiting examples of haploid inducer lines that can be used to repeat the experiments below include Stock 6 (Coe 1959), RWS (Rober et al. 2005, KEMS (Deimling et al. 1997), KMS or ZMS (Chalyk et al. 1994; Chalyk and Chebotar 2000), or other inducer lines derived from these. The inducer line may also carry at least one marker trait to facilitate the identification of haploid offspring. The purity of the haploid pool can be made to be 95% or greater and can be verified using a variety of methods known in the art.

Example 1. A Single Unsubmerged Spin with the Plant Treatment Agent Colchicine Successfully Improves Doubling Efficiency Corn seeds of four different maize F1 hybrid-derived haploid induction populations were used in this experiment; two of the populations, Male 1 and Male 2, were derived from two different male inbred lines and the remaining two populations, Female 1 and Female 2, were derived from two different female inbred lines. Seeds of each germplasm were germinated in soil and the subsequent seedlings tended in a greenhouse under standard maize growing conditions until the seedlings reached the V1 to V2 growth stages.

Next, several randomly-selected seedlings of each germplasm were then removed from the soil, washed to remove residual soil and then subjected to a contacting step which included soaking the seedlings for 10 minutes in a liquid doubling agent comprising 1250 ppm colchicine.

After the contacting step, seedlings were bundled in a PCS with wooden rods, similar to that described in FIG. 9. The seedlings and rods were wrapped tightly together with several layers of aluminum foil. Care was taken to wrap the seedlings tightly, but not so tight as to damage the tissues of the seedling. The folds and layers of the wrap were arranged such that any liquid agent still clinging to the surface of the plant would not be trapped inside the wrap during centrifugation.

Once arranged in the centrifuge, seedlings were subjected to an unsubmerged centrifugation at 335 g for 3 min.

After centrifugation, the seedlings were removed from the centrifuge container, rinsed with water to remove any remaining plant treatment agent, and then transplanted into 10-inch pots in a growth room where they were tended under standard maize growing conditions until they grew to maturity and flowered.

Self-pollinations were attempted with each plant that survived the treatment to produce pollen and during the ensuing growth the pollination success, fertilization success and final doubling efficiency were determined within each sample.

Control samples of several randomly-selected seedlings from each germplasm received no exposure to the plant treatment agent, but were otherwise handled identically as their treated counterparts.

Table 1 reveals that all control plants failed to produce pollen. Consequently, they could not be selfed or produce selfed seed, and so yielded a DE of zero. On the other hand, all samples receiving the unsubmerged centrifugation treatment exhibited good overall seed set and average population DEs ranging from 42% to 71%, depending on the germplasm.

TABLE 1

Effects on DH success when diverse haploid maize germplasms are subjected to a single unsubmerged centrifugation. Pollination Successes are the number of plants that produced silks and pollen and so could be selfed; Fertilization Successes are the number of doubling-treated haploid plants that produced an ear with at least one seed. DE is the doubling efficiency, equal to the fertilization success divided by the number of plants treated within each germplasm and treatment.

| Group | Treated | Pollination Successes | Fertilization Successes | DE |
|---|---|---|---|---|
| Treated Male1 | 14 | 13 | 10 | 71% |
| Treated Male2 | 15 | 12 | 10 | 67% |
| Treated Female1 | 19 | 10 | 8 | 42% |
| Treated Female2 | 8 | 6 | 4 | 50% |
| Control Male1 | 12 | 0 | 0 | 0% |
| Control Male2 | 14 | 0 | 0 | 0% |
| Control Female1 | 13 | 0 | 0 | 0% |
| Control Female2 | 11 | 0 | 0 | 0% |

This example demonstrates that these methods effectively deliver doubling agents to plant meristems and increase doubling efficiencies over current methods in a wide range of maize germplasms. In certain embodiments, other plant treatment agents could be delivered to a wide range of alternative tissues in additional maize germplasms and in species other than maize. Whenever delivery of a chemical agent to a specific plant tissue is desired, especially if the tissue is difficult to reach because it is internal or covered and/or protected by other tissues, like a shoot meristem, these methods will provide more success than those using current methods.

Colchicine is toxic, so a 10 min soak was chosen for the contacting step in this example, and it revealed a dramatic difference in DE. It is understood that depending on the age of the plants, the centrifuge speed, concentration of colchicine, and/or other parameters, contacting steps comprising longer or shorter duration might be optimized to achieve desired results under other conditions.

Example 2. A Single Submerged Centrifugation with the Plant Treatment Agent Colchicine Successfully Improves Doubling Efficiency Seeds of 5 different F1 hybrid-derived haploid commercial corn lines were randomly-selected and germinated in a greenhouse. The resulting seedlings were removed from soil or growth media at the V1-V2 growth stage and the soil or growth media rinsed from the plants with water. One sample of several random seedlings within each haploid line was placed in a centrifuge sample container without regard to how the shoot-root axis of the plants would be orientated with respect to the force of acceleration generated during the planned centrifugation. Next, a plant treatment solution comprising 1000 ppm colchicine was poured into the container such that the solution submerged each plants SAM, and then the sample centrifuged at 50 g for 10 min with the SAMs submerged in the plant treatment agent.

Following centrifugation, the plants were removed, rinsed with water to remove any remaining colchicine solution, and then recovered and tended in a light, humidity, and temperature-controlled greenhouse for several days before being transplanted to a nursery greenhouse.

The control sample received no centrifugation or colchicine exposure, but was otherwise handled identically as the treatment sample. During the subsequent growth of the plants, the initial survival, pollination success, fertilization success, and doubling efficiency (DE) were determined within each sample.

Every inbred line subjected to contact with the plant treatment agent during centrifugation showed large improvements in pollination success, fertilization success, and DE as compared to their corresponding untreated controls (Table 2). The overall average DE improved by 25% in the centrifuged samples with only a 15% drop in initial survival as compared to their controls. It was also noted that for every sample, the initial survival equaled the final survival and that while at least 25% of all individuals in the inbred samples receiving the experimental treatment produced pollen and silks, 3 of those same 5 inbreds had a 0% pollination success when they received the control treatment.

TABLE 2

Results of subjecting diverse haploid genotypes to a single submerged centrifugation. Pollination Successes are the number of plants that produced silks and pollen and so could be selfed; Fertilization Successes are the number of doubling-treated haploid plants that produced an ear with at least one seed. DE is the doubling efficiency, equal to the fertilization success divided by the number of plants treated within each germplasm and treatment.

| Centrifugation | Inbred Line | Total Plants Treated | Initial Survival | Poll. Success | Fert. Success | DE |
|---|---|---|---|---|---|---|
| Submerged | F1004 | 14 | 100% | 50% | 100% | 50% |
| | F1045 | 12 | 58% | 43% | 100% | 25% |
| | F1095 | 15 | 87% | 69% | 78% | 47% |

TABLE 2-continued

Results of subjecting diverse haploid genotypes to a single submerged centrifugation. Pollination Successes are the number of plants that produced silks and pollen and so could be selfed; Fertilization Successes are the number of doubling-treated haploid plants that produced an ear with at least one seed. DE is the doubling efficiency, equal to the fertilization success divided by the number of plants treated within each germplasm and treatment.

| Centrifugation | Inbred Line | Total Plants Treated | Initial Survival | Poll. Success | Fert. Success | DE |
|---|---|---|---|---|---|---|
| | F1118 | 10 | 40% | 25% | 100% | 10% |
| | F1900 | 10 | 100% | 50% | 40% | 10% |
| | Ave: | | 77% | 47% | 84% | 30% |
| None (control) | F1004 | 14 | 93% | 0% | 0% | 0% |
| | F1045 | 12 | 92% | 0% | 0% | 0% |
| | F1095 | 15 | 87% | 15% | 50% | 7% |
| | F1118 | 10 | 100% | 0% | 0% | 0% |
| | F1900 | 10 | 90% | 22% | 100% | 10% |
| | Ave: | | 92% | 7% | 30% | 5% |

These data reveal that a single submerged centrifugation treatment effectively delivers plant treatment agents to the tissues of plants. In this case, a doubling agent was effectively delivered to the meristems of haploid plants with the effect of drastically the improving doubling efficiency of those plants with very little impact on plant survival.

Example 3. A Serial Centrifugation Treatment Successfully Improves Doubling Efficiency Seeds of 5 different F1 hybrid-derived haploid corn lines were randomly-selected and germinated in a greenhouse. The resulting seedlings were removed from soil or growth media at the V1-V3 growth stage and the soil or growth media rinsed from the plants with water. Seedlings were then aligned and assembled along with several rods in a bundled PCS similar to what is shown in FIG. 9 and a plant treatment solution comprising 1000 ppm colchicine was poured into the container such that the solution submerged the SAM of each plant and then the entire sample was centrifuged at 50 g for 3 min while the SAMs remained submerged in the plant treatment agent.

Following the first centrifugation, the plant treatment solution was decanted and the seedlings subjected to an unsubmerged centrifugation at 335 g for 3 min. During the second centrifugation, the PCS and seedlings were aligned such that SAMs of each plant did not contact the reserve treatment agent during application of the centrifugal force.

Following the second centrifugation, the plants were removed from the centrifugation container and rinsed with water to remove any remaining colchicine solution, and then recovered and tended in a light, humidity, and temperature-controlled greenhouse for several days before being transplanted to a nursery greenhouse.

The control sample received no colchicine exposure, but was otherwise handled identically as the experimental samples. During the subsequent growth of the plants, the initial survival, pollination success, fertilization success, final survival, and doubling efficiency was determined within each sample as described in Example 2.

All five genotypes subjected to the serial centrifugation showed significantly improved pollination success, fertilization success, and doubling efficiency with no decrease in initial survival as compared with their corresponding untreated controls (Table 3). For every sample, the initial survival equaled the final survival. A 67% increase in overall DE among the samples receiving the experimental treatment as compared to their controls was observed. Furthermore, while at least 62% of all individuals in the inbred samples receiving the experimental treatment produced pollen and silks, 3 of those same 5 inbreds generated 0% pollination success when they received the control treatment.

Table 3. Results of subjecting diverse haploid genotypes to a first submerged centrifugation followed by a second, unsubmerged centrifugation. Pollination Successes are the number of plants that produced silks and pollen and so could be selfed; Fertilization Successes are the number of doubling-treated haploid plants that produced an ear with at least one seed. DE is the doubling efficiency, equal to the fertilization success divided by the number of plants treated within each germplasm and treatment.

TABLE 3

Results of subjecting diverse haploid genotypes to a first submerged centrifugation followed by a second, unsubmerged centrifugation. Pollination Successes are the number of plants that produced silks and pollen and so could be selfed; Fertilization Successes are the number of doubling-treated haploid plants that produced an ear with at least one seed. DE is the doubling efficiency, equal to the fertilization success divided by the number of plants treated within each germplasm and treatment.

| Centrifugation | Inbred Line | Total Plants Treated | Initial Survival | Poll. Success | Fert. Success | DE |
|---|---|---|---|---|---|---|
| Double | F1004 | 14 | 93% | 62% | 100% | 57% |
| | F1045 | 12 | 100% | 75% | 100% | 75% |
| | F1095 | 15 | 100% | 87% | 92% | 80% |
| | F1118 | 10 | 70% | 100% | 86% | 60% |
| | F1900 | 10 | 100% | 100% | 90% | 90% |
| | Ave: | | 93% | 85% | 94% | 72% |
| None | F1004 | 14 | 93% | 0% | 0% | 0% |
| | F1045 | 12 | 92% | 0% | 0% | 0% |
| | F1095 | 15 | 87% | 15% | 50% | 7% |
| | F1118 | 10 | 100% | 0% | 0% | 0% |
| | F1900 | 10 | 90% | 22% | 100% | 10% |
| | Ave: | | 92% | 7% | 30% | 5% |

These data reveal that the serial centrifugation treatment effectively delivers plant treatment agents to the tissues of plants. In this case, a doubling agent was effectively delivered to the meristems of haploid plants with the effect of drastically the improving doubling efficiency of those plants with essentially no impact on survival.

Example 4. Other Plant Treatment Agents

To demonstrate the ability of centrifugation to aid the delivery of plant treatment agents to plant tissues, the plant growth regulator uniconazole (a gibberelic acid inhibitor) in the form of the commercial mix Sumagic® (0.055% uniconazole) was mixed in a plant treatment solution and contacted by plants subjected to centrifugation.

Three samples of F1-derived haploid corn plants at V1-3 growth stage each were subjected to a single submerged centrifugation at 50 g for 10 min during which the SAMs of each plant remained in contact with a reserve treatment agent comprising either a) an inactive plant treatment solution containing no Sumagic (the control), b) a plant treatment solution containing an additional 1% (vol:vol) Sumagic, or c) a plant treatment solution containing an additional 2%.

Following centrifugation, the plants were removed, rinsed with water to remove any remaining plant treatment agent, and then recovered and tended in a light, humidity, and temperature-controlled greenhouse for several days before being transplanted to a nursery greenhouse. After three weeks of growth, each plant was visually assessed for its ability to survive its respective treatment. FIG. 1 shows exemplary representatives of the plants recovered from each of the three treatments.

FIG. 1 reveals that samples centrifuged while contacted with 1% or 2% Sumagic were shorter, exhibited larger leaves that were darker in color, exhibited thicker stems, and exhibited more root biomass. This suggests not only the ability of these methods to provide efficient delivery of plant treatment agents other than doubling agents to plant tissues, but also that the addition of growth regulators in the treatment solution can improve plant health.

Example 5. Plants Display Surprising Survivability in Field Settings

Haploid corn seedlings derived from a cross between commercial inbred 01DKD2 and the inducer KHI1 or commercial inbred 83IDI1 and KHI1 were treated by either single spin or serial spin centrifugation methods and recovered in a light, moisture, and temperature controlled environment for approximately 15 hours. Plants were then transplanted into a field and tended for three weeks, after which plant survival rates were assessed (Table 5).

TABLE 5

Field transplanting survival rates of two inbred-derived haploid lines following single submerged or serial spin centrifugation treatments in combination with three different treatment solutions with different colchicine concentrations.

| Haploid Parent | [Colchicine] (ppm) | First Spin (submerged) | Second Spin (unsubmerged) | Plants Treated | 3-wk Survival |
|---|---|---|---|---|---|
| 83IDI1 | 1000 | 10 min, 50 g | none | 100 | 81% |
|  | 1250 | 3 min, 50 g | 3 min, 335 g | 99 | 83% |
|  | none | 3 min, 50 g | 3 min, 335 g | 49 | 98% |
|  | none | 10 min, 50 g | none | 51 | 98% |
| 01DKD2 | 1000 | 10 min, 50 g | none | 99 | 94% |
|  | 1250 | 3 min, 50 g | 3 min, 335 g | 99 | 89% |
|  | none | 3 min, 50 g | 3 min, 335 g | 50 | 96% |
|  | none | 10 min, 50 g | none | 48 | 100% |

Table 5 reveals that haploid corn lines derived from two genetically divergent inbreds demonstrate excellent survival rates when transplanted into field settings after treatment. The 3 week post transplanting survival rate of either haploid line was higher than 80% regardless of the colchicine concentration or whether a second spin was applied.

Example 6. Plants can Survive Strong Centrifugation Forces Followed by Field Transplanting Haploid seedlings from several different F1 hybrid-derived haploid induction populations were grown in a greenhouse to the V1-V2 stage, at which time they were removed from the soil, rinsed with water to remove residual soil, divided into two samples of an equal number of plants, and then each sample was bundled together along with several rods into two PCSs similar to that shown in FIG. 9. The plants were then subjected to a submerged centrifugation at 50 g for 3 min while the SAMs remained submerged in the treatment agent.

Following the first submerged centrifugation, the seedlings were subjected to a slower and shorter unsubmerged centrifugation for 3 min at 335 g and the other sample subjected to a faster and longer unsubmerged centrifugation for 10 min at 500 g.

Following centrifugation, all seedlings were removed from the centrifuge container, rinsed with water to remove any remaining plant treatment agent, and then transplanted to an outdoor maize field where they were tended under standard maize growing conditions until they grew to maturity and flowered. Self-pollinations were attempted with each plant that survived the treatment well enough to produce pollen and silks and during the ensuring growth the number of kernels that formed on each ear and on each plant was recorded. Survival rates of all seedlings subjected to the same treatment were combined across all germplasms and averaged to yield an overall survival rate within each treatment. Similarly, the doubling efficiencies among all germplasms were combined and averaged to yield an overall DE within each treatment.

TABLE 6

Average survival rates and doubling efficiencies among inbreds of diverse germplasms subjected to one of two different unsubmerged centrifugations treatments as part of an overall serial centrifugation treatment.

| Second Centrifugation | Final Field Survival Rate | DE |
|---|---|---|
| 3 min @ 335 g | 67% | 26% |
| 10 min @ 500 g | 63% | 25% |

This example demonstrates that users can obtain both excellent delivery of treatment agents to targeted tissues (as evidenced by the high DEs) and excellent survival rates even when plants are transplanted directly to the field following treatment. Furthermore, it demonstrates that substantially increasing the duration and speed of centrifugation, as compared to other examples herein, wherein centrifugation treatments are typically 3 min at 335 g, has little effect on survival rates and doubling efficiencies. It is thus anticipated that other centrifugation durations and times will be useful among a wide range of centrifugation parameters and post-treatment plant recovery methods (e.g. direct field transplanting vs. growth chamber, etc.).

Example 7. Delivery of Treatment Agents and Good Survival is Possible Among a Wide Range of Plant Growth Stages To demonstrate this how these methods can be sued among a wide range of plant growth stages, haploid plants were subjected to an identical serial centrifugation treatment comprising a first submerged centrifugation followed by a second unsubmerged centrifugation. Three different growth stages and the effects on DH-related success indicators between the three life stages were compared.

F1 hybrid-derived haploid seedlings derived from either female inbred line 91DUQ1 or male inbred line 83IDI1 were germinated in soil in a greenhouse in standard maize growing conditions. To ensure that the older seedlings would fit into the centrifuge sample container, and to ensure that all seedlings received the same chemical treatments, all seedlings were subjected to a 1% paclobutrazol (PBZ) soil drench treatment at 6 days after planting, 10 ml per plant.

This population of seedlings was subdivided into 3 samples, each comprising several dozen seedlings. Half of the seedlings in each sample were derived from 91DUQ1 and the other half derived from 83IDI1. A first sample was removed from the soil at the V1-V2 growth stage (1 week after planting), a second sample removed from the soil at the V3-V4 stage (2 weeks after planting) and a third sample removed from the soil at the V4-V5 growth stage (3 weeks after planting).

Following removal from the soil, seedlings in each sample were rinsed in water to remove residual soil, then wrapped in a PCS along with several wooden rods, similar that that shown in FIG. 9, and subjected to a first submerged centrifugation in 1250 ppm colchicine at 50 g for 3 min.

Following the first, submerged centrifugation, the plant treatment solution was decanted. The seedlings, with some residual agent clinging to their surfaces, were returned to the empty centrifuge container and subjected to a unsubmerged centrifugation at 335 g for 3 min.

Following the second centrifugation, the plants were removed from the centrifugation container and rinsed with water to remove any remaining colchicine solution, and then recovered and tended in a light, humidity, and temperature-controlled greenhouse for several days before being transplanted to a nursery green house where they were tended under standard maize growing conditions until they grew to maturity and flowered.

Self-pollinations were attempted with each plant that survived the treatment to produce pollen and silks and during the ensuing growth the pollination success, fertilization success and final doubling efficiency were determined within each sample. In this experiment, the doubling efficiency within each growth stage sample was calculated by dividing the number of plants that produced at least one ear comprising at least four kernels by the total number of plants treated.

Figure 4:
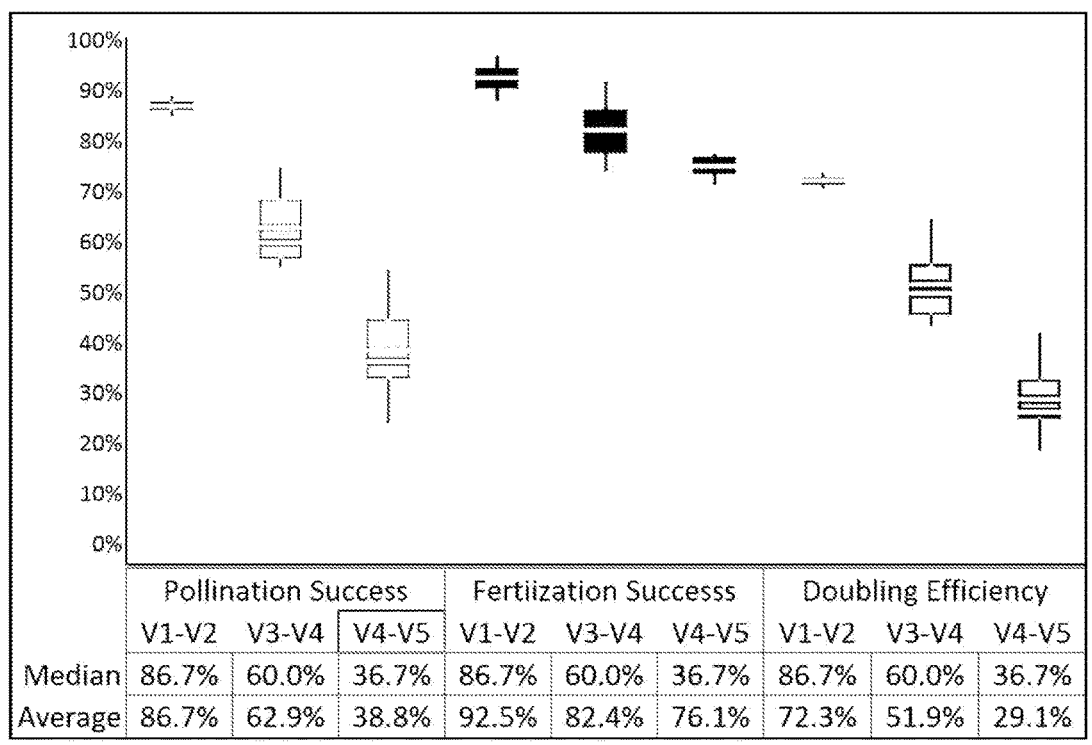
FIG. 4 shows improved pollination success, fertilization success, and doubling efficiencies achieved by aided delivery of plant treatment agents to plants at different life stages.

One clear trend in FIG. 4 is that samples treated at earlier life stages tend to exhibit higher pollination success, fertilization success, and doubling efficiency. However, it is noted that the data clearly testify to the utility of using these methods on plants at least up through V4-V5, as that growth stage sample here yielded good scores in all three criteria evaluated. Particularly encouraging is the fact that the doubling efficiency of this group averaged almost 30%, with a median of 36.7%, revealing that these methods can be used to deliver doubling agents to older plants as well, at least as high as V6.

FIG. 4 also clearly suggests that these methods can be used to deliver doubling agents to plants much younger than V1, as the V1-V2 sample exhibited a DE of over 70%. It is expected that this trend of effective agent delivery to targeted tissues in young plants could extend to as early in the life cycle as the point when germination first begins. These data also reveal that these methods could be used on even younger plants by employing methods known in the art for excising embryos from seeds prior to germination (e.g. embryo rescue) or by employing a method of penetrating the seed coat with a treatment agent to facilitate contact between an un-germinated plant and a treatment agent.

Example 8. Plants can Survive Very Strong Centrifugation Forces

F1 hybrid-derived haploid seedlings derived from either female corn inbred line 91DUQ1 or male corn inbred line 83IDI1 were germinated in soil in a greenhouse in standard maize growing conditions and grown to the V1-V2 growth stage (1 week after planting). Seedlings were then removed from the soil, rinsed to remove residual soil, and partitioned into 5 samples comprising several dozen seedlings each.

The plants of one sample were bundled together, along with several wooden rods, into a PCS similar to that shown in FIG. 9. This bundled PCS sample was placed into a centrifuge container, roots first. Each plant of the other four samples were individually wrapped to a PCS comprising a rod with a paraffin wrap and placed into a separate centrifuge container, one plant-PCS assembly per container, similar to that shown in FIG. 7.

Once attached to their respective PCSs and placed into their respective centrifuge containers, a solution comprising 1250 ppm colchicine was added to each container until each plant was submerged at least up until the SAM of every plant was submerged. All samples were then centrifuged with the SAMs submerged in treatment solution for 3 min at 50 g.

Following the first centrifugation, the treatment solution was drained from each centrifugation container, and then each sample was subjected to an unsubmerged spin for 3 minutes at one of six different rates, ranging from 340 g to 2000 g, as shown in Table 9.

Following the second centrifugation, the plants were removed from the centrifugation container and rinsed with water to remove any remaining colchicine solution, and then transplanted into 10-inch pots and tended in a growth room under standard maize growing conditions until they grew to maturity and flowered.

Self-pollinations were attempted with each plant that survived the treatment to produce pollen and an ear, and pollination success as determined within each sample.

TABLE 7

Comparison of five different centrifugation speed treatments on haploid plant samples. Initial survival is the portion of plants that survived to flowering. Pollination Success is the number of plants that produced pollen and silks and so could be selfed; Fertilization Success is the number of doubling-treated haploid plants that produced an ear with at least one seed. DE is the doubling efficiency, equal to the fertilization success divided by the number of plants treated within each germplasm and treatment.

| Treatment | Unsubmerged Centrifugation Force | Survival Rate | Pollination success | Fertilization Success | DE |
|---|---|---|---|---|---|
| Individually-wrapped | 340 g | 92.9% | 100.0% | 96.2% | 89.3% |
|  | 500 g | 96.4% | 100.0% | 100.0% | 96.4% |
|  | 750 g | 87.5% | 100.0% | 95.2% | 83.3% |
|  | 1000 g | 92.9% | 92.3% | 100.0% | 85.7% |
|  | 2000 g | 72.7% | 100.0% | 87.5% | 63.6% |
| Bundled | 340 g | 90.0% | 90.0% | 85.0% | 68.9% |

Table 7 reveals that even plants centrifuged at 2000 g for 3 min exhibited excellent survival rates. It also reveals that excellent doubling rates and consistent results were obtained when plants were individually supported by a PCS during centrifugation.

Thus, it is reasonable to conclude that these methods will be useful for speeds above 2000 g and that a user could expect to recover at least some $DH_1$ seeds using a broad range of centrifugation rates, including at least as high as 4000 or 5000 g, although higher centrifugation rates might still produce acceptable results.

Example 9. The Efficiency of Plant Treatment Agent Delivery can be Optimized with Incubations This experiment demonstrated that an incubation step between centrifugations can improve delivery of plant treatment agents.

F1 hybrid-derived haploid seedlings derived from either female inbred line 91DUQ1 or male inbred line 83IDI1 were germinated in soil in a greenhouse in standard maize growing conditions and grown to the V1 growth stage (1 week after planting). Next, the seedlings were removed from the soil, rinsed with water to remove residual soil form the plants, and then divided into 4 samples comprising several seedlings of each germplasm per sample.

Each sample was then bundled in a PCS comprising an aluminum foil wrap and wooden rods for support, similar to that shown in FIG. 9. Once bundled in a PCS, each sample was contacted by a plant treatment solution comprising either 600 ppm or 800 ppm colchicine such that the SAM of each plant was entirely submerged, and then each sample was centrifuged at 100 g for 3 min with the SAMs submerged in the reserve doubling agent during centrifugation.

Following the submerged centrifugation, plants were removed from the centrifuge container and while some doubling solution from the first centrifugation remained clinging to the plants, the roots and bottom half of each stem were rinsed in water to remove any doubling agent from that end of the plant. Then each bundled sample was incubated in an enclosed, humid environment for one of the four incubation periods listed Table 8.

Following each respective incubation period, the bundled samples were removed from the humid enclosure and subjected to an unsubmerged centrifugation at 340 g for 3 min, wherein the only doubling solution that contacted the plants was that which remained on the plants from the previous submerged centrifugation, i.e. no additional doubling solution was added to the plants after the first centrifugation.

Following the second centrifugation, the plants were removed from the centrifugation container and rinsed with water to remove any remaining colchicine solution, and then recovered and tended in a light, humidity, and temperature-controlled greenhouse for several days before being transplanted to a nursery green house where they were tended under standard maize growing conditions until they grew to maturity and flowered.

Self-pollinations were attempted with each plant that survived the treatment to produce pollen and final doubling efficiencies were determined within each treatment. In this experiment, the doubling efficiency within each treatment sample was calculated by dividing the number of plants of each treatment sample that produced at least one ear comprising at least four kernels by the total number of plants subjected to that set of treatment conditions.

Table 8 reveals that good doubling efficiencies were obtained with increasing incubation periods, even at relatively low concentrations of plant treatment agent.

TABLE 8

The effects on doubling efficiencies of four different treatment combinations comprising two different plant treatment agent concentrations and two different incubation periods on haploid plants. Plants were subjected to a first submerged centrifugation at a plant treatment agent (colchicine) concentration of either 600 or 800 ppm, followed by an incubation period of either 3 min or 3 hrs, and then subjected to an unsubmerged centrifugation.

| [Treatment Agent] ppm | Incubation Period | DE |
|---|---|---|
| 600 | 3 min | 0.41 |
| 600 | 3 hrs | 0.78 |
| 800 | 3 min | 0.66 |
| 800 | 3 hrs | 0.79 |

Table 8 reveals that these methods are useful among a wide range of plant treatment concentrations and incubation periods wherein plants are in contact with a plant treatment agent. These results are consistent with the conclusion that incubation periods before or between centrifugation steps can improve delivery of plant treatment agents to target tissues. In certain embodiments, a user can contact a plant with a plant treatment agent and then purposely delay a subsequent centrifugation in order to achieve improved doubling efficiencies.

Example 10. A Broad Range of Centrifugation Durations are Effective with this Invention Seedlings of one of two genetically diverse inbred lines (83IDI1 or 91DUQ1) were germinated in a greenhouse and removed from soil or growth media at the V1-V3 growth stage and rinsed with water to remove residual soil. All seedlings were then secured in PCSs comprising wraps and rods, like that shown in FIG. 9, and subjected to a submerged spin at 50 g in a liquid treatment solution comprising 1250 ppm colchicine for 3 min.

Following the first, submerged centrifugation, the plant treatment solution was decanted and the bundled seedlings were subjected to an unsubmerged centrifugation at 340 g for either 3 or 180 min.

Following the second centrifugation, the plants were removed from the centrifugation container and rinsed with water to remove any remaining colchicine solution, and then recovered and tended in a light, humidity, and temperature-controlled greenhouse for one week, then the number of plants surviving were counted to determine the survival rate within each treatment.

TABLE 10

Survival rates of seedlings of two different germplasms subjected to unsubmerged centrifugations for two different durations.

| Pedigree | Centrifugation Duration (minutes) | Survival |
|---|---|---|
| 83IDI1 | 3 | 93% |
| 83IDI1 | 180 | 94% |
| 91DUQ1 | 3 | 95% |
| 91DUQ1 | 180 | 96% |

Table 10 reveals that centrifugation times can be dramatically increased without lowering the survival rates, even among diverse germplasms. Even at 3-hour spins, this method yields excellent survivability. It is thus clear that these methods are very effective over broad centrifugation ranges, testifying to their utility when used with centrifugation durations beyond those directly tested herein.

What is claimed is:

1. A method of delivering a plant treatment agent to a cell of a selected tissue of a plant, wherein the plant has a surface, wherein the selected tissue is located at, and/or beneath, a portion of the plant surface, the method comprising contacting the plant surface with a solution that comprises the plant treatment agent, including contacting plant tissue other than the selected tissue, and applying a centrifugal force to the plant to transport the solution that comprises the plant treatment agent to the selected tissue, wherein the plant is supported inside a centrifuge container by a plant centrifugation support such that the shoot-root axis of the plant is aligned with the direction of the centrifugal force during centrifugation, wherein the plant centrifugation support comprises a structural support separate from the wall or walls of the centrifugation container, wherein the plant has germinated, and wherein the centrifugal force applied is from about 10 g to about 4,000 g,
thereby delivering the plant treatment agent to the cell of the selected tissue of the plant.

2. The method of claim 1, wherein at least 5% of the plant surface remains in contact with the solution that comprises the plant treatment agent during the application of the centrifugal force, and wherein the centrifugal force is applied from about 10 g to about 500 g.

3. The method of claim 1, wherein the selected tissue remains in contact, by use of a plant centrifugation support, with the solution comprising the plant treatment agent that is not absorbed by the plant during the application of the centrifugal force, during at least a portion of the application of the centrifugal force, and wherein the centrifugal force is applied from about 10 g to about 500 g.

4. The method of claim 1, wherein the selected tissue is maintained separated, by use of a plant centrifugation support, from the plant treatment agent not absorbed by the plant during the application of the centrifugal force, during at least a portion of the application of the centrifugal force.

5. The method of claim 1, wherein the plant treatment agent is a polynucleotide.

6. A method of creating a doubled-haploid corn plant by delivering a chromosome doubling agent to a cell of a shoot meristem tissue, the method comprising contacting a $DH_0$ mother plant with a solution that comprises the chromosomal doubling agent, including contacting plant tissue other than shoot meristem tissue, and applying a centrifugal force to the $DH_0$ mother plant,
wherein the plant is supported inside a centrifuge container by a plant centrifugation support such that the shoot-root axis of the plant is aligned with the direction of the centrifugal force during centrifugation,
wherein the plant centrifugation support comprises a structural support separate from the wall or walls of the centrifugation container,
thus delivering the solution that comprises the chromosome doubling agent to the cell of the shoot meristem tissue, wherein the corn plant has germinated.

7. The method of claim 6, wherein the doubling efficiency resulting from the delivery of the chromosome doubling agent is increased in comparison to delivering the chromosome doubling agent to the cell of the shoot meristem tissue by only contacting the $DH_0$ mother plant with the solution that comprises the chromosome doubling agent without application of the centrifugal force.

8. The method of claim 6, wherein the centrifugal force applied is from about 10 g to about 500 g.

9. The method of claim 6, wherein the shoot meristem tissue is maintained in contact, by use of a plant centrifugation support, with the solution comprising the chromosome doubling agent that is not absorbed by the plant during the application of the centrifugal force, during at least a portion of the application of the centrifugal force.

10. The method of claim 6, wherein the shoot meristem tissue is maintained separated, by use of a plant centrifugation support, from the chromosome doubling agent not absorbed by the plant during the application of the centrifugal force, during at least a portion of the application of the centrifugal force.

11. The method of claim 6, wherein the corn plant is in the VE, V1, V2, V3, V4, or V5 vegetative growth stage.

12. A method for delivering a plant treatment agent to a cell of a selected tissue of a plant, wherein the plant has a surface, wherein the selected tissue is located at, and/or beneath, a portion of the plant surface, the method comprising the steps of:
(a) contacting the surface of the plant with a solution comprising the plant treatment agent, wherein the plant has germinated;
(b) applying a centrifugal force to the plant in step (a) contacted with the solution,
wherein the plant is supported inside a centrifuge container by a plant centrifugation support such that the shoot-root axis of the plant is aligned with the direction of the centrifugal force during centrifugation,
wherein the plant centrifugation support comprises a structural support separate from the wall or walls of the centrifugation container;
(c) following the application of the centrifugal force in step (b), removing the plant from the centrifugal force and treatment solution; and
(d) applying a subsequent centrifugal force to the plant subjected to the centrifugal force in step (b), thereby delivering the plant treatment agent to the plant tissue.

13. The method of claim 12, wherein the selected tissue remains in contact, by use of a plant centrifugation support, with the solution comprising the plant treatment agent that is not absorbed by the plant during the application of the centrifugal force, during at least a portion of the application of the centrifugal force in step (b) and wherein the centrifugal force is applied from about 10 g to about 4000 g.

14. The method of claim 12, wherein the selected tissue is maintained separated, by use of a plant centrifugation support, from the plant treatment agent not absorbed by the plant during the application of the centrifugal force, during at least a portion of the application of the centrifugal force in step (b), and wherein the centrifugal force is applied from about 10 g to about 4000 g.

15. The method of claim 12, wherein during the application of centrifugal force in step (d), the plant is supported inside a centrifuge container by a plant centrifugation support such that the shoot-root axis of the plant is aligned with the direction of the centrifugal force during centrifugation and wherein the plant centrifugation support comprises a structural support separate from the wall or walls of the centrifugation container.

16. The method of claim 1, wherein the plant centrifugation support prevents the plant from being damaged by the force generated during centrifugation.

17. The method of claim 6, wherein the plant centrifugation support prevents the plant from being damaged by the force generated during centrifugation.

18. The method of claim 12, wherein the plant centrifugation support prevents the plant from being damaged by the force generated during centrifugation.

19. The method of claim 15, wherein the plant centrifugation support prevents the plant from being damaged by the force generated during the application of centrifugal force in step (d).

* * * * *